(12) United States Patent
Harding et al.

(10) Patent No.: US 10,926,000 B2
(45) Date of Patent: Feb. 23, 2021

(54) DEPOSITION-CONVERSION METHOD FOR TUNABLE CALCIUM PHOSPHATE COATINGS ON SUBSTRATES AND APPARATUS PREPARED THEREOF

(71) Applicant: Colorado School of Mines, Golden, CO (US)

(72) Inventors: Jacqueline L. Harding, Golden, CO (US); Melissa D. Krebs, Englewood, CO (US)

(73) Assignee: Colorado School of Mines, Golden, CO (US)

(*) Notice: Subject to any disclaimer, the term of this patent is extended or adjusted under 35 U.S.C. 154(b) by 0 days.

(21) Appl. No.: 15/595,310

(22) Filed: May 15, 2017

(65) Prior Publication Data

US 2017/0326272 A1 Nov. 16, 2017

Related U.S. Application Data

(60) Provisional application No. 62/337,179, filed on May 16, 2016, provisional application No. 62/336,006, filed on May 13, 2016.

(51) Int. Cl.

| | |
|---|---|
| *A61L 27/32* | (2006.01) |
| *C08G 65/34* | (2006.01) |
| *C08F 16/06* | (2006.01) |
| *C08L 5/08* | (2006.01) |
| *C08L 5/04* | (2006.01) |

(Continued)

(52) U.S. Cl.
CPC ............. *A61L 27/32* (2013.01); *A61L 27/54* (2013.01); *C01B 25/26* (2013.01); *C08F 16/06* (2013.01); *C08G 65/34* (2013.01); *C08L 5/04* (2013.01); *C08L 5/08* (2013.01); *C08L 71/02* (2013.01); *A61K 31/7088* (2013.01); *A61K 33/42* (2013.01); *A61L 2420/02* (2013.01); *C08F 16/10* (2013.01)

(58) Field of Classification Search
CPC ...... A61F 1/24; A61F 2/44; A61F 2/28; A61F 2/2846; A61L 27/00
USPC .......... 3/1; 623/17.16, 16.11, 23.51; 606/77; 427/2.24, 2.26, 2.27
See application file for complete search history.

(56) References Cited

U.S. PATENT DOCUMENTS 3,869,731 A * 3/1975 Waugh ...................... A61F 2/38
                                                            623/20.21
4,465,794 A    8/1984 Kuzma
(Continued)

FOREIGN PATENT DOCUMENTS

| WO | WO 96/13284   | 5/1996 |
|----|---------------|--------|
| WO | WO 2009/028965 | 3/2009 |

OTHER PUBLICATIONS

"ChronOS® Bone Void Filler," DePuySynthes, 2014, 8 pages.
(Continued)

*Primary Examiner* — Dah-Wei D. Yuan
*Assistant Examiner* — Andrew J Bowman
(74) *Attorney, Agent, or Firm* — Sheridan Ross PC

(57) ABSTRACT

The present invention relates to a method for in situ biomimetic mineralization of polymeric hydrogels, where the incorporated CaP phase can be selectively tuned in chemical composition and morphology to mimic bone and dental mineral. The present invention also relates to a method to coat a substrate with apatite material, the resulting product and the use of the product.

20 Claims, 23 Drawing Sheets

(51) Int. Cl.

| | |
|---|---|
| C01B 25/26 | (2006.01) |
| A61L 27/54 | (2006.01) |
| C08L 71/02 | (2006.01) |
| C08F 16/10 | (2006.01) |
| A61K 33/42 | (2006.01) |
| A61K 31/7088 | (2006.01) |

(56) References Cited

U.S. PATENT DOCUMENTS

| | | | |
|---|---|---|---|
| 4,619,995 | A | 10/1986 | Hayes |
| 5,147,344 | A | 9/1992 | Sachau et al. |
| 5,370,692 | A | 12/1994 | Fink et al. |
| 6,733,503 | B2 * | 5/2004 | Layrolle ............ A61F 2/30767 427/2.24 |
| 7,682,540 | B2 | 3/2010 | Boyan et al. |
| 2004/0236432 | A1 * | 11/2004 | Hyon ...................... A61L 27/34 623/23.51 |
| 2005/0082710 | A1 | 4/2005 | Oriakhi et al. |
| 2006/0134160 | A1 | 6/2006 | Troczynski et al. |
| 2007/0098799 | A1 | 5/2007 | Zhang et al. |
| 2008/0241353 | A1 * | 10/2008 | Liu ......................... A61L 27/32 427/2.27 |
| 2010/0021544 | A1 | 1/2010 | Bourges et al. |
| 2010/0035838 | A1 | 2/2010 | Heber et al. |
| 2011/0160861 | A1 * | 6/2011 | Jimenez ............. A61B 17/7065 623/17.16 |
| 2013/0045182 | A1 | 2/2013 | Gong et al. |
| 2013/0211522 | A1 * | 8/2013 | Weiss ................. A61B 17/8095 623/16.11 |
| 2014/0312535 | A1 | 10/2014 | Dikovsky et al. |
| 2015/0257936 | A1 | 9/2015 | Lowing |
| 2016/0346429 | A1 | 12/2016 | Krebs et al. |
| 2018/0171304 | A1 | 6/2018 | Beyer et al. |
| 2018/0235739 | A1 | 8/2018 | Jahn |
| 2018/0243980 | A1 | 8/2018 | Erb et al. |
| 2018/0298215 | A1 | 10/2018 | Andersen et al. |

OTHER PUBLICATIONS

"HydroSet Injectable Bone Substitute," brochure, Stryker, 2014, 6 pages.

"PRO-DENSE® Graft-Bone Graft Substitute," Wright, 2015, retrieved from https://web.archive.org/web/*/http://www.wright.com/physicians/prodense/product-overview, 2 pages.

Bleek et al., "New developments in polymer-controlled, bioinspired calcium phosphate mineralization from aqueous solution," Acta Biomaterialia, 2013, vol. 9(5), pp. 6283-6321, 2 pages, abstract only.

Dorozhkin et al., "Biological and Medical Significance of Calcium Phosphates," Angewandte Chemie, 2002, vol. 41(17), pp. 3130-3146, abstract only, 2 pages.

Elliott, "Mineral, synthetic and biological carbonate apatites," Structure and Chemistry of the Apatites and Other Calcium Orthophosphates (book), Elsevier, 1994, pp. 191-304, 1 pages, abstract only.

Harding et al., "Controlled and Tunable Biomimetic Apatite Mineralization of Synthetic Hydrogels," Macromolecular Materials and Engineering, 2016, 3 pages, abstract only.

Hassan et al., "Structure and Applications of Poly(vinyl alcohol) Hydrogels Produced by Conventional Crosslinking or by Freezing/Thawing Methods," Advanced Polymer Science, 2000, vol. 153(37), pp. 37-65.

John et al., "A trial to prepare biodegradable collagen-hydroxyapatite composites for bone repair," Journal of Biomaterials Science-Polymer Edition, 2001, vol. 12, pp. 689-705, abstract only, 2 pages.

Kumar et al., "Transformation of modified brushite to hydroxyapatite in aqueous solution: effects of potassium substitution," Biomaterials, 1999, vol. 20(15), pp. 1389-1399, 2 pages, abstract only.

Oonishi et al., "Clinical Application of Hydroxyapatite in Orthopedics," Advances in Calcium Phosphate Biomaterials, Chapter 2, 2014, pp. 19-49.

Raynaud et al., "Calcium phosphate apatites with variable Ca/P atomic ratio I. Synthesis, characterisation and thermal stability of powders," Biomaterials, 2002, vol. 23(4), pp. 1065-1072, 1 page, abstract only.

Rezwan et al., "Biodegradable and bioactive porous polymer/inorganic composite scaffolds for bone tissue engineering," Biomaterials, 2006, vol. 27(18), pp. 3413-3431, 1 page, abstract only.

Schweizer et al., "Polymer-Controlled, Bio-Inspired Calcium Phosphate Mineralization from Aqueous Solution," Macromolecular Bioscience, 2007, vol. 7(9-10), pp. 1085-1099, abstract only, 2 pages.

Surmenev, "review of plasma-assisted methods for calcium phosphate-based coatings fabrication," Surface & Coatings Technology, 2012, vol. 206, pp. 2035-2056.

Yang et al., "Artificial hydroxyapatite film for the conservation of outdoor marble artworks," Materials Letters, 2014, vol. 124, pp. 201-203, abstract only, 2 pages.

Zadpoor, "Relationship between in vitro apatite-forming ability measured using simulated body fluid and in vivo bioactivity of biomaterials," Materials Science and Engineering: C, 2014, vol. 35, pp. 134-143, abstract only, 2 pages.

Official Action for U.S. Appl. No. 15/170,630 dated Oct. 3, 2017, 9 pages, Restriction Requirement.

Official Action for U.S. Appl. No. 15/170,630 dated Jan. 30, 2018, 12 pages.

Doyle et al., "Collagen Automated Mineralization Printer," Northeastern University Department of Mechanical and Industrial Engineering, Dec. 6, 2016, 58 pages.

Markstedt et al., "3D Bioprinting Human Chondrocytes with Nanoceltulose-Alginate Bioink for Cartilage Tissue Engineering Applications," BioMacromolecutes, 2015, pp. 1489-1496 (Abstract 2 pages).

Official Action for U.S. Appl. No. 15/170,630 dated Jun. 11, 2018, 15 pages.

Official Action for U.S. Appl. No. 15/170,630 dated Oct. 22, 2018, 16 pages.

Official Action for U.S. Appl. No. 15/170,630 dated Jun. 7, 2019, 18 pages.

Ex Parte Quayle Action for U.S. Appl. No. 15/832,562, dated May 2, 2019, 6 pages.

Ju et al., "NanoBioSensing: Principles, Development and Application," 2011, Springer, New York, NY, p. 140.

Rodrigues et al., "Calcium phosphate nanoparticles functionalized with dimethacrylate monomer," Materials Science and Engineering C, vol. 45, Sep. 8, 2004, pp. 122-126.

Official Action for U.S. Appl. No. 15/170,630 dated Jan. 7, 2020, 18 pages.

Notice of Allowance for U.S. Appl. No. 15/170,630, dated May 22, 2020, 10 pages.

Corrected Notice of Allowance for U.S. Appl. No. 15/170,630, dated Jul. 20, 2020, 6 pages.

Official Action for U.S. Appl. No. 16/256,352, dated Apr. 28, 2020, 16 pages.

Notice of Allowance for U.S. Appl. No. 15/832,562, dated Jul. 17, 2019, 6 pages.

* cited by examiner

DEPOSITION-CONVERSION METHOD FOR TUNABLE CALCIUM PHOSPHATE COATINGS ON SUBSTRATES AND APPARATUS PREPARED THEREOF

CROSS REFERENCE TO RELATED APPLICATIONS

This application claims priority under 35 U.S.C. § 119(e) to U.S. Provisional Application Ser. No. 62/337,179, filed May 16, 2016, and U.S. Provisional Application No. 62/336,006, filed on May 13, 2016. Each of these references are incorporated by reference in their entirety.

FIELD OF THE INVENTION

The present invention is related to a method to form and deposit calcium phosphate coatings on the surface of a substrate, and the resulting apparatus thereof. The calcium phosphate coatings can be specifically tuned for particular applications.

BACKGROUND

The application of calcium phosphate (CaP) coatings onto a substrate is currently achieved by high temperature plasma spray or extended immersion in aqueous buffers. Each method lacks control over the resulting CaP composition or morphology. Existing technologies rely on synthetically derived CaP phases not recognized by the physiological environment.

Early CaP materials were titanium implants functionalized with a deposited hydroxyapatite coating, and now there are numerous commercial CaP formulations available on the market as void fillers and synthetic grafting materials. Inspired by the composite nature of hard tissues, mineralized hydrogels are interesting materials to explore as synthetic bone grafts. While hydrogels are well established for their versatility as cellular growth templates, the regenerative potential of hydrogels to be used for osteoconduction has been shown to be enhanced with the addition of CaP mineral phase. The composition, morphology, and resorbability of CaP materials are known to be contributing factors to the efficacy of CaP materials in regenerative applications. To date, the formulation of synthetic graft materials has yet to rival the efficacy of natural bone grafts. As a bioactive interface, the exact chemistry of CaP coatings ideally would match the composition of the tissue it is replacing, leading to increased interest in the rational design of CaP based materials towards mimicking native bone mineral composition.

The biosynthesis of apatite during hard tissue formation is a stepwise process where an amorphous CaP phase is initially deposited onto collagen fibrils and undergoes slow conversion to apatite in the physiological milieu, illustrated in FIG. 1. Biosynthesized apatites found in bone, dentin, and enamel are poorly crystalline carbonated apatite particles that exhibit distinct variations in ionic composition and particle morphology attributed to the specific function of each tissue. In particular, bone apatite is found to grow in longitudinal plates directed by the adsorption of citrate molecules, in contrast to enamel formed as rod shaped particles with high degree of surface fluoride substitution important for improved resistance to dental carries.

Biomineralization is the process by which bones and teeth are formed through the nucleation of CaP polymorphs, principally apatite, onto the surface of collagen. To mimic the composition of mineralized tissues, synthetic grafts and bone void fillers are frequently formulated to include CaP polymorphs intended to improve biocompatibility and osteoconductivity of biomaterials. The biological performance of CaP materials is associated with fundamental parameters including chemical composition, morphology, and resorbability of the CaP polymorph. However, to date, there has not been a method available that provides control over the resulting CaP polymorphs within mineralized biopolymers. For tissue engineering applications, ideal CaP-composite materials would include biomimetic CaP polymorphs in place of the synthetic hydroxyapatite currently used.

The integration of implanted biomaterials with the host environment is largely contingent upon the surface properties of the implanted material. CaP polymorphs based on the analogous composition of bone and dental tissue are frequently utilized as coatings applied to biomaterials. CaP-based materials are found to improve the biocompatibility of implantable materials by inhibiting encapsulation with fibrous tissue and ultimately promoting integration of the implant with surrounding tissues. Hydroxyapatite (HA) is the most frequently used CaP analogue in biomaterial production, however as HA is a non-resorbable highly crystalline polymorph, materials prepared with HA lack the potential for promoting regenerative effects.

CaP coatings have been deposited on implantable materials with methodologies that can be categorized as thermal spray, vapor, and wet deposition. Thermal spray and vapor approaches are advantageous for the deposition of thick, uniform CaP coatings typically consisting of HA. However, the success of these deposition approaches requires a robust substrate that can withstand harsh synthetic conditions including high temperatures and pressures. Polymeric substrates are very important for the construction of biomaterials and are best suited to apply coatings under mild conditions. Wet deposition methods take place in aqueous and non-aqueous mediums alike and can be tuned for mild reaction conditions. The typical approach for the biomimetic mineralization of apatite on substrates involves extended immersion in simulated body fluid (SBF). Polymeric materials of natural or synthetic origin and metallic substrates alike can be coated using wet deposition. However, this method remains unsatisfactory due to low deposition yields and a lack of control over the final CaP composition and morphology. In summary, the direct deposition of apatite as a substrate coating is often cumbersome, and it is difficult to tune the composition, morphology, and coating thickness of the resulting phase.

Current methods to form CaP coated substrates, such as the method illustrated in FIG. 1, lack synthetic control at the interface for chemical composition, particle morphology, and homogenous dispersion of the resulting CaP phase. There is a need for the development of a mild wet chemistry approach for the rapid and selective synthesis of apatite coatings on polymeric hydrogels. The present invention addresses these shortcomings.

SUMMARY

The present invention is directed to a rapid, efficient, and tunable method for depositing CaP coatings on the surface of substrates. CaP coatings are effective at improving the biocompatability of implantable materials since CaP is an important component in the construction of bone mineral.

Through imitation of biomineralization processes, the coating of substrates in the present invention is achieved according to a novel process. In a first step, an easily transmutable phase is deposited on a substrate surface. In the second step, the coated substrate is exposed to aqueous conditions analogous to physiological conditions, which results in the transformation of the initially deposited CaP coating to biomimetic apatite. Tuning of the resulting apatite phase to correspond with the composition of bone and dental mineral is achieved via solution additives. The coating methodology has been applied to polymeric substrates of synthetic and natural origin. The deposition onto polymeric surfaces is effective for improving the biocompatibility of existing biomaterials. Furthermore, the CaP-coating method has been extended to collagen substrates successfully, thus fully mimicking biomineralization processes.

The preparation of materials where the CaP coating is tuned on an application specific basis has the potential to enhance successful integration of implants within biological environments reducing material rejection, and in the case of bone grafts promoting healthy tissue growth. For example, CaP coatings are used frequently to improve the interfacial responses of implantable materials with biological systems. Evidence indicates that the closer in composition the deposited CaP phase is to naturally formed CaP, the higher the biological activity. This results in minimized foreign body response, enhanced integration of materials with native tissue, and the potential for regeneration of damaged tissue in the case of use as a synthetic bone graft. Current methodologies for coating substrates with CaP lack control over the resulting mineral phase, reaction conditions denature substrates, or thin coatings deposited after lengthy reaction times (weeks-months).

One aspect of the present invention is a calcium phosphate substrate precursor. The precursor includes a substrate coated with calcium ions and phosphate ions.

The phosphate source for the phosphate ions is selected to reduce or eliminate the incorporation of undesirable ions into the precursor. Another aspect of the present invention is a tunable calcium phosphate substrate precursor. The precursor comprises a substrate, where the substrate is coated with calcium ions and phosphate ions in the form of Dicalcium Phosphate Dihydrate (DCPD).

Another aspect of the present invention is a calcium phosphate material. The material includes a substrate, wherein a material of the substrate is synthetic or non-synthetic and a calcium phosphate coating. The calcium phosphate coated is tunable.

Yet another aspect of the present invention is a method to deposit calcium phosphate on a substrate. The method includes immersing the substrate in a calcium ion solution, then immersing the calcium coated substrate in water. Next, the substrate is immersed in a phosphate ion solution. The substrate can then be immersed in an alternating fashion in the calcium ion solution and the phosphate ion solution to prepare a coated substrate. Next, the coated substrate is hydrolyzed under physiological conditions to form calcium phosphate.

Still another aspect of the present invention is a calcium phosphate material. The material includes a substrate. The substrate is synthetic or non-synthetic. The calcium phosphate coating on the substrate is tunable.

DETAILED DESCRIPTION

Figure 1:
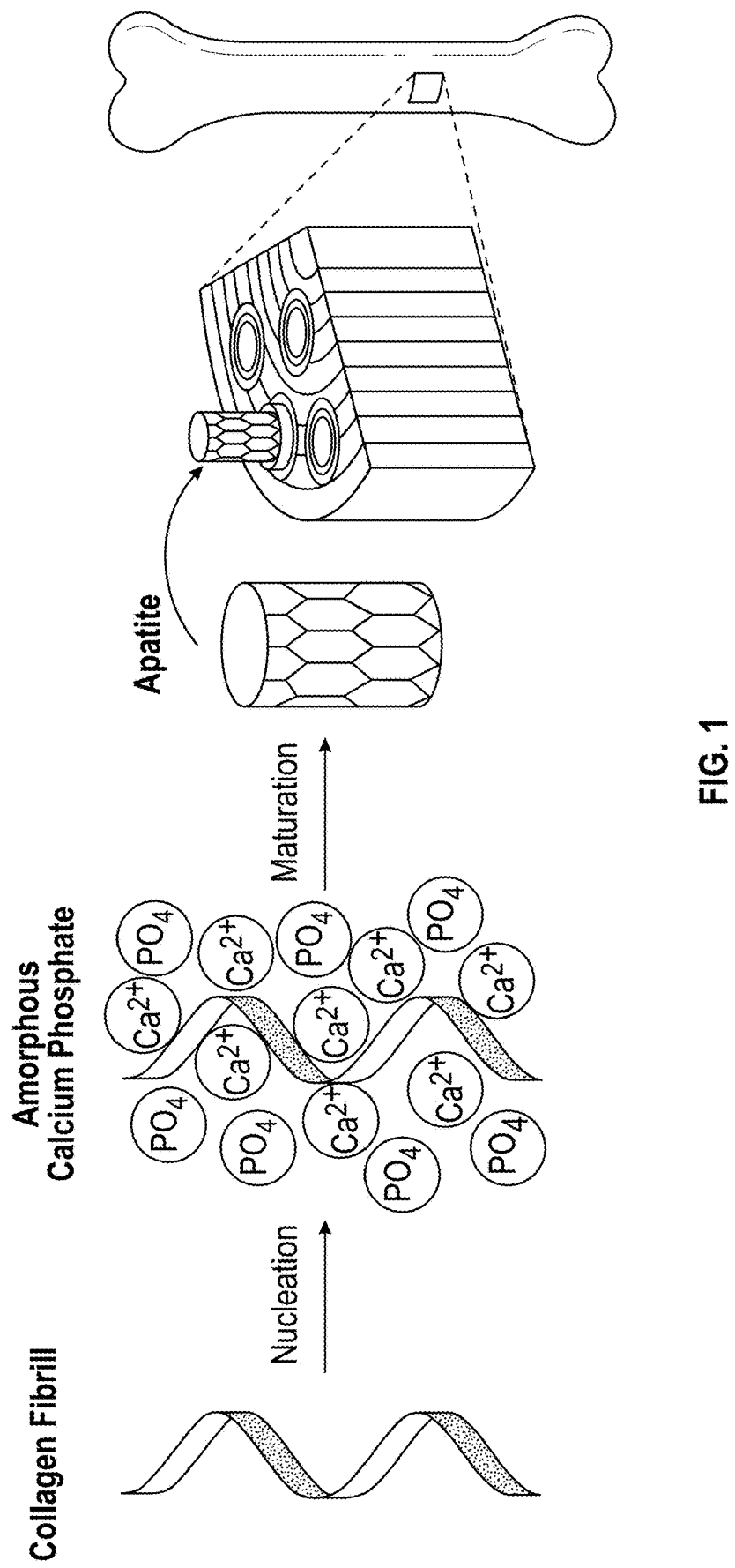
FIG. 1 illustrates the prior art methods of synthesis of apatite coatings deposited onto organic substrates by biomineralization of collagen fibrils with apatite resulting from the conversion of initially deposited amorphous calcium phosphate.
Figure 2:
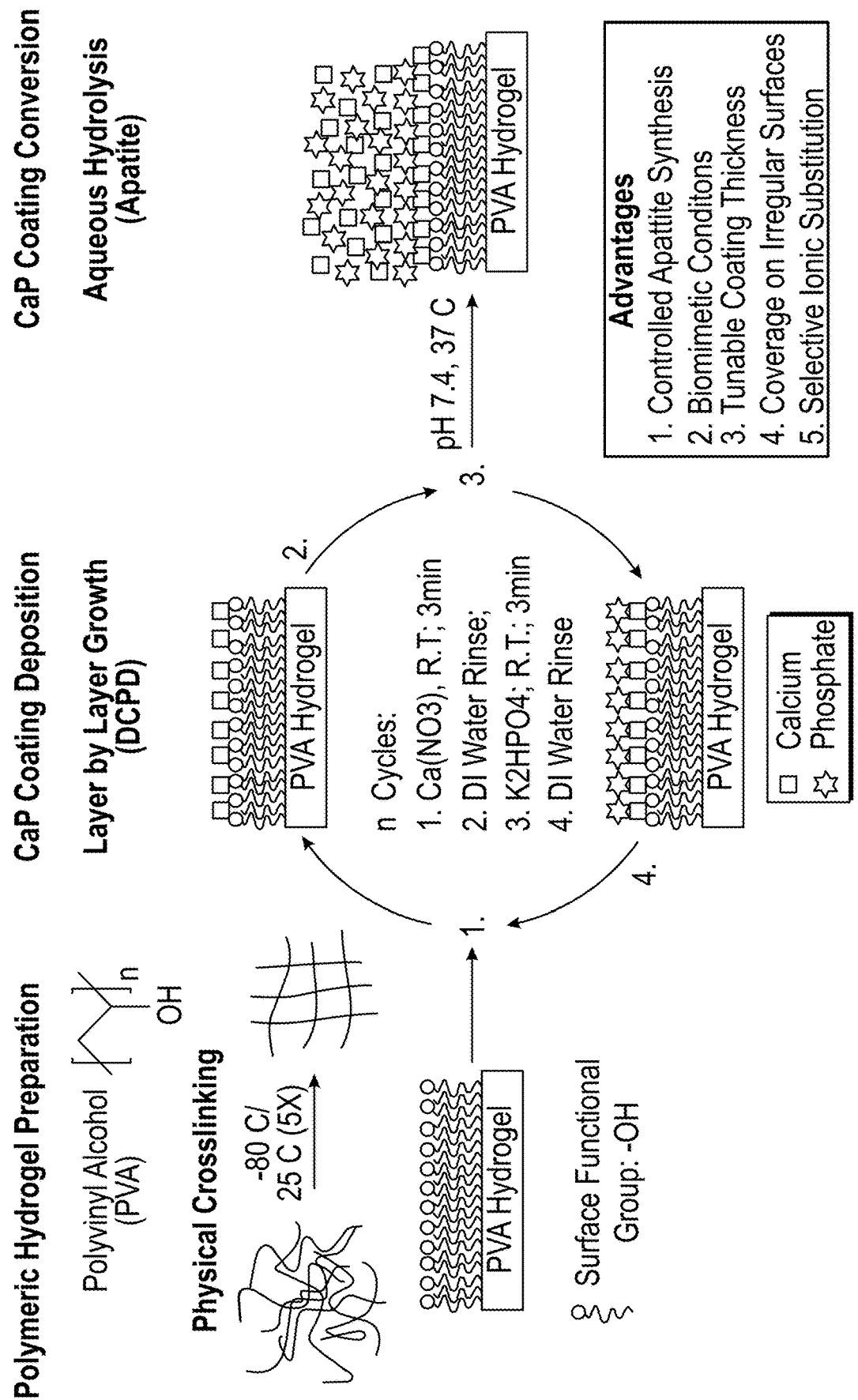
FIG. 2 illustrates the synthesis of apatite coatings deposited onto organic substrates by the biomimetic deposition-conversion approach of the present invention for the preparation of tunable apatite coatings on synthetic hydrogels.

The present invention is generally related to a two-step wet coating method where DCPD is deposited on a surface and subsequently matured to apatite. An overview of the wet coating method of the present invention is illustrated in FIG. 2.

One aspect of the present invention is a DCPD deposition process by immersion of the substrate in calcium and phosphate ion solutions at a temperature between about 22° C. and about 50° C. resulting in the surface growth of DCPD crystals on the substrate, In some embodiments, the temperature can be about room temperature (which is about 25° C.).

In some embodiments, the substrate coated with the DCPD crystals can be further processed. The substrate can be subjected to aqueous hydrolysis under physiological conditions where the pH is between about 6 and about 10, in some embodiments about 7.4, and a temperature between about 25° C. and about 50° C., in some embodiments about 37° C. Following aqueous hydrolysis, the CaP can be transformed into apatite. The resulting composition of apatite phase can be tuned based on the ionic composition of the conversion buffer solution. By way of example, carbonate and fluoride can be incorporated into the final apatite lattice to mimic the formulation of bones and teeth. The method of the present invention is far superior to existing technology because it facilitates direct control over the composition, morphology, and amount of the final CaP polymorph deposited on the substrate surface.

Furthermore, the present invention can be applied to organic and inorganic substrates including hydrophilic polymeric materials of synthetic and natural origin including, but not limited to, PVA, PEG, chitosan, cellulose, alginate, and collagen, and combinations thereof. Polymeric substrates can be formulated as hard or soft polymers with various surface topologies and crosslinked as hydrogels. The present invention can also be applied and used with inorganic substrates such as silica, titanium, gold, stainless steel and combinations thereof. Substrates that resist CaP coatings can first be coated with polydopamine to promote CaP deposition on the surface of the material. The CaP coatings can be coated with polydopamine by preparing an aqueous solution of dopamine and placing the substrate in the solution at a temperature between about 22° C. and about 50° C., in some embodiments about room temperature, for a time period between about 8 hours and about 48 hours, in some embodiments about 12 hours or overnight. The concentration of the dopamine can be between about 0.05M and about 0.5M. In general, coating material surfaces with CaP promotes cell attachment and cell response.

Figure 3:
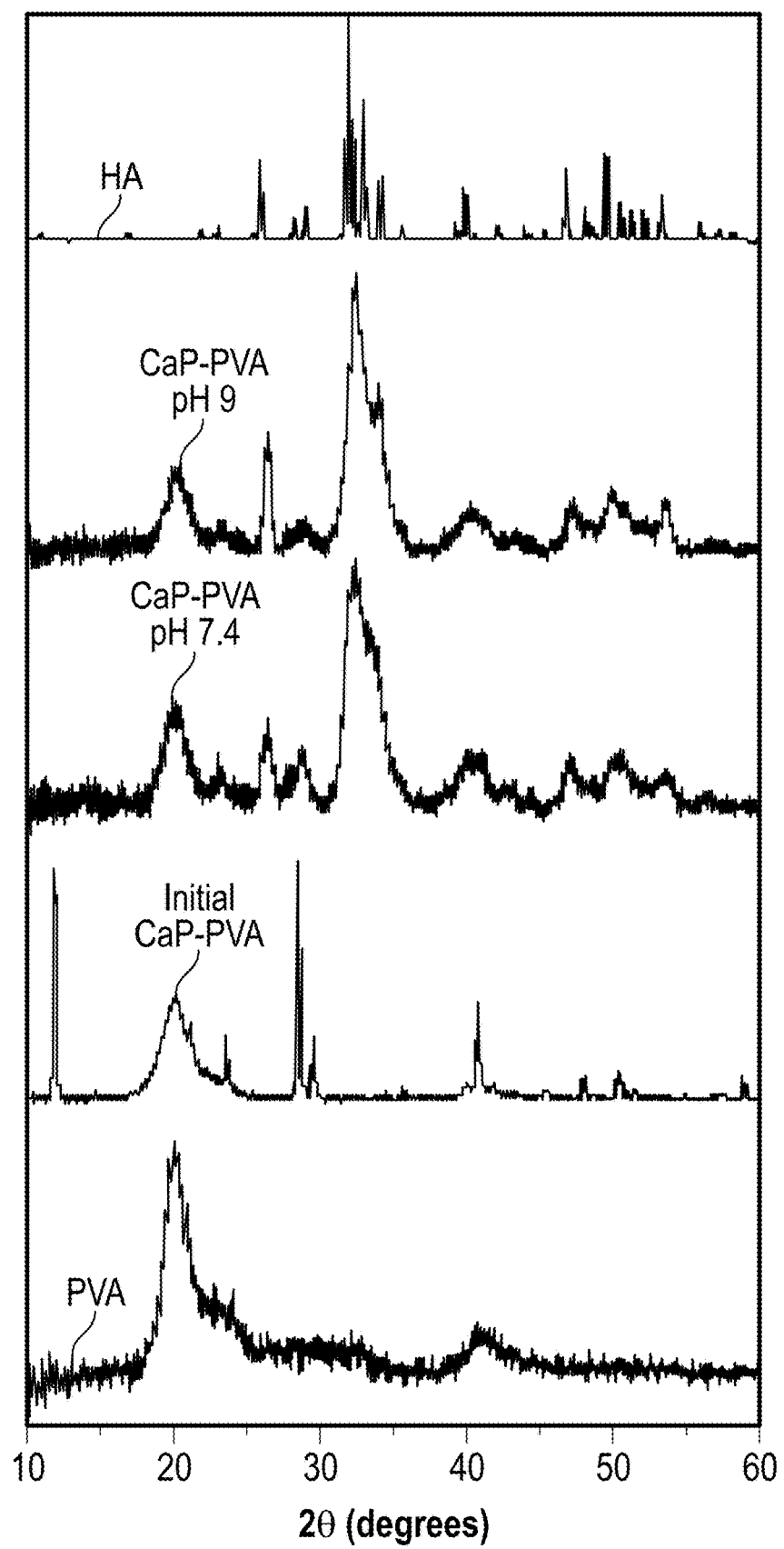
FIG. 3 illustrates an XRD pattern of CaP-PVA materials.
Figure 4:
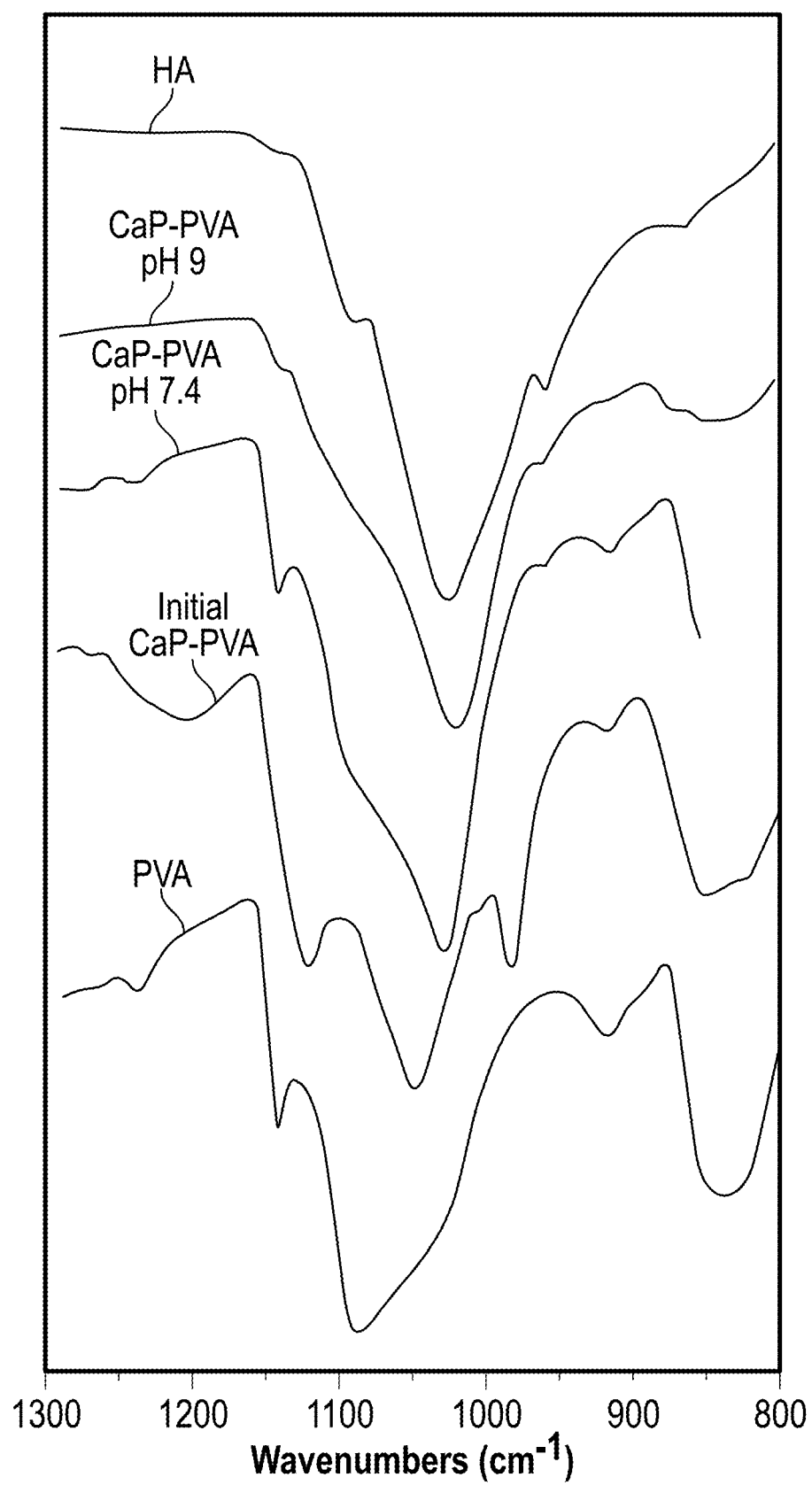
FIG. 4 illustrates an FTIR pattern of CaP-PVA materials.

The chemical composition and morphology of the CaP particles incorporated into the hydrogel can be confirmed with X-ray diffraction (XRD) and infrared spectroscopy (IR), and scanning electron microscopy (SEM). The CaP polymorphs incorporated in the polymeric hydrogel before and after hydrolysis were analyzed by XRD and IR as illustrated in FIGS. 3 and 4, respectively. The initial CaP phase incorporated into the polymeric matrix is unequivocally identified as DCPD. Subsequent hydrolysis at pH about 7.4 and about 9 resulted in the transformation of the DCPD to apatite. Notably, the morphology of the incorporated apatite phase was found to differ based on the hydrolysis solution pH. DCPD can be converted to large interconnected crystals at pH about 7.4 compared to individual spherical particles at pH about 9 as illustrated in FIG. 2. The variations in particle morphology were determined to be a result of a pH-dependent hydrolysis pathway, where at pH 7.4 the formation of octacalcium phosphate (OCP) as a transition state was necessary, while at pH 9 direct conversion to apatite was seen.

Notably, the method of the present invention results in a biomineralization mechanism that correlate with reported biomineralization mechanisms where biological apatite can be formed from an unstable CaP precursor phase using OCP as an intermediate. Thus, the method of the present invention facilitates the formation of biomimetic CaP composite materials that can be easily tuned for specific applications. Advantageously, the method can result in a tunable pore structure for the directed deposition of the mineral phase as an exclusive surface coating or simultaneous penetration of the bulk interior and the deposition of exterior surface coatings. The pore structure, or morphology, can be tuned to a particle shape, a petal like shape, a plate like shape, or a spherical crystal shape.

Furthermore, in some embodiments, the method can further facilitate the preparation of carbonated and fluoride doped lattices intended to mimic the natural composition of bone and dental apatites, respectively.

Formation of Hydrogels

An aspect of the invention is a method to form a hydrogel. The hydrogel can be formed by combining PVA in an aqueous solution. The aqueous solution can be water, a buffer solution, including zwitterionic biological buffer, Good's buffer, HEPEs buffer, Tris buffer, carbonate buffer, and the like. The amount of PVA can be controlled such that the hydrogel contains between about 5 wt. % and about 20 wt. % of PVA. The weight percent of PVA is relative to the amount of PVA and solution used during the formation of the hydrogel or polymer. For example, a 10 wt. % PVA hydrogels can be formed by adding about 25 g of PVA to 225 mL of water.

The hydrogel is formed by cyclic freezing/thawing at temperatures between about −20° C. and about −80° C. for the freezing temperature, in some embodiments about −80C, and between about 1° C. and about 30° C. for the thawing temperature, in some embodiments about 25° C. The hydrogel is maintained at temperature for between about 10 minutes and about 48 hours. The freeze/thaw cycle is repeated for between 1 and 100 cycles, in some embodiments about 5 cycles.

In some embodiments, a collagen hydrogel can be formed. Collagen, between about 0.25 wt. % and about 0.75 wt. %, in some embodiments about 0.5 wt. % in an acid solution. The acid solution can be acetic acid, hydrochloric acid, sulfuric acid, phosphoric acid, citric acid, or other suitable acids. The concentration of acid can be between about 0.025 M and about 0.1 M, in some embodiments about 0.05M. The collagen solution can be kept in an ice bath to prevent denaturing. Separately a solution of chondroitin sulfate, between about 0.25 mg and about 0.7 mg, in some embodiments about 0.5 mg, was prepared in between about 50 mL and about 150 mL, in some embodiments about 100 mL, of acetic acid. The concentration of acetic acid can be between about 0.05 M and about 0.1 M. Chondroitin solution can be added to the collagen solution while homogenizing. In some embodiments, the chondroitin solution can be added dropwise or slowly to the collagen solution. Once completely homogenized, the collagen/chondroitin sulfate solution can be degassed under vacuum for between about 5 minutes and about 24 hours in some embodiments about 60 minutes, to remove bubbles introduced during homogenization. The duration can depend upon the solution volume. Then the collagen solution can be frozen at a temperature between about −190° C. and about −10° C., in some embodiments about −20° C. for between about 1 minute and about 36 hours, in some embodiments about 24 hours. Upon removal from the freezer the material can be lyophilized for between about 60 minutes and about 96 hours, in some embodiments about 72 hours. The lyophilized collagen substrates can be dehydrothermally crosslinked in a vacuum oven at between about 100° C. and about 125° C., in some embodiments about 105° C. for between about 60 minutes and about 36 hours, in some embodiments about 24 hours.

Deposition of Dicalcium Phosphate Dihydrate (DCPD) by Alternate Immersion

Immature CaP phase DCPD is deposited as a coating onto prefabricated polymeric substrates by the alternating immersion in Calcium salt solution and Phosphate salt solution. The concentration of each salt solution is between 0.1M and 0.5M under acidic conditions. The ratio of calcium salt to phosphate salt is irrelevant because the salt solutions are never combined. The substrate is exposed to the salt solutions has less reactive sites than ions in solution. Therefore, the salt solution concentrations are always in excess. The acidic condition is present because the formation of DCPD necessitates a solution pH between about 3 and about 6. The pH of the solution was modified by the addition of an acid with spectator ions that cannot be incorporated into the mineral lattice such as HCl, sulfuric acid, or nitric acid. For this purpose, it is essential to avoid the use of phosphoric or carboxylic acids to adjust pH such as but not limited to acetic, citric, or oxalic acid. The substrate does not need to be fully hydrated prior to use. If the substrate is hydrated, then it can enable the mineralization of the interior (if the pore structure supports this) compared to only the outer surface of the material.

If the substrate is a hydrogel, then the hydrogels can be hydrated by soaking in Millipore water, a calcium solution or a phosphate solution. The soaking duration can depend upon the substrate used and the swelling capacity and/or the hydrophilicity of the substrate. Some substrates hydrate within about a minute, while others might take about 24 hours to hydrate. In some embodiments, the substrate might not hydrate at all. The mineralization procedure on any substrate can be performed at a temperature between about 20° C. and about 50° C., in some embodiments about room temperature. Heating can promote the rate of hydrating the substrate. Mineralized substrates can be soaked in a suitable amount of calcium solution, for example calcium nitrate, dependent upon the size of the substrate, which can vary from very small substrates (i.e. a nanoparticle) to very large substrates (i.e. a boat). The substrate can be soaked in the calcium solution for less than about 1 minute and greater than about 60 minutes, in some embodiments 3 minutes. The concentration of calcium solution, for example calcium nitrate, can be between about 0.05 M and about 0.5 M, in some embodiments about 0.25 M. The products are removed and rinsed with Millipore water. Next, the hydrogels were soaked in a potassium solution, for example $K_2HPO_4$, for less than about 1 minute and greater than about 60 minutes, in some embodiments about 3 minutes. The concentration of $K_2HPO_4$ can be between about 0.05 M and about 0.5 M, in some embodiments about 0.25 M. Alternate immersion of the substrate was performed between 1-100 cycles, in some embodiments about 20 cycles. The calcium and phosphate ion solutions can be refreshed at any time. Deposition of a white mineral phase may be noted after the first cycle. The deposited mineral phase can increase with successive cycles, with a corresponding increase in the rigidity of the mineral phase.

In some embodiments, the coating can be applied to prefabricated substrates. The substrates can originate from cast molds, electrospinning, 3D printing applications or other prefabrication methods.

In some embodiments, the method can be used to deposit a thickness of DCPD, which can correlate with particular properties, control particle morphologies, and particle composition. The thickness can be between about 5 microns to about 500 microns.

Hydrolysis of DCPD to Biomimetic Apatite Derivatives

Hydrolytic conversion of DCPD deposited on the substrates to apatite was accomplished by soaking the mineralized hydrogels in a sufficient amount of solution to submerge the mineralization surface of the substrate. In some embodiments, the solution can be a tris buffer solution. The tris buffer solution can be adjusted to pH of between about 7 and about 10, in some embodiments about 7.4 with a basic solution, for example NaOH. The tris buffer solution can be maintained at a temperature between about 25° C. and about 50° C., in some embodiments about 37° C. In some embodiments, the pH of the buffer solution can be maintained at about 7.4 by the periodic addition of 1M NaOH. Modification of the maturation buffer to incorporate substituting ions can be achieved by the direct addition of ionic salts to the solution. Suitable ionic salts include, but are not limited to, magnesium, sodium, fluoride, chlorine, citrate, carbonate, calcium, phosphate or combinations thereof. The amount of ionic salt can be dependent upon the volume used. For example, for fluoride treated substrates, NaF can be added to the buffer solution equal to between about 0.001 M and about 0.05 M, in some embodiments about 0.025M. Simulated body fluid as an immersion buffer can be between about 1 and about 3.5 times the normal body fluid concentration. In some embodiments about 50 mM tris buffer solution can be used as a buffer solution.

Method to Coat a Polymer with DCPD

An aspect of the invention is a method to coat a polymer with DCPD. The method comprises soaking a polymer in a calcium salt solution, followed by rinsing the polymer with water. Next, the polymer is soaked in a phosphate solution, then rinsed with water to form the polymer coated with DCPD.

The calcium salt can be any suitable soluble calcium salt, including but not limited to, calcium chloride, calcium nitride, and the like. The concentration of the calcium salt in solution can be between about 0.2M and about 1M. The polymer can be soaked in the calcium salt solution for between about 1 minute to about 60 minutes, in some embodiments about 3 minutes. If the polymer is a hydrogel, it can equilibrate with environment. The soaking temperature can be between about 20° C. and about 50° C., in some embodiments about room temperature. In some embodiments, the calcium solution can include an additive. Suitable additives include, but are not limited to, carbonate, citrates, sodium, magnesium, fluoride, simulated body fluid, calcium ions, phosphate ions, and mixed ionic solution to form simulated body fluid, or simulated saliva and combinations thereof. The additive can be added to a solution, for example a tris buffer solution, or can be included without a solution. The concentration of the additive in the calcium solution can be between about 0.05 M and about 0.5 M, in some embodiments about 0.25 M. Furthermore, the calcium solution can be reused, but can be replaced once the solution becomes cloudy.

Water can be used at several steps in the method. The water can be deionized, distilled, or tap.

The phosphate source in the phosphate solution can be a dibasic phosphate compound. Suitable dibasic phosphate compounds include but are not limited to, dipotassium phosphate, ammonium phosphate, phosphoric acid and combinations thereof. The phosphate source can be chosen to reduce or eliminate the incorporation of undesirable ions into the biological apatite. For example, ammonia phosphate does not incorporate ions into the biological apatite product sourced from the ammonia phosphate. The concentration of phosphate can be the same as the concentration of the calcium in the calcium solution. In some embodiments, the concentration of phosphate can be between about 0.2M and about 1M. The polymer can be soaked in the phosphate solution for between about 1 minute and about 60 minutes, in some embodiments about 3 minutes. The soaking temperature can between about 20° C. and about 50° C., in some embodiments about room temperature. Furthermore, the phosphate solution can be reused, but can be replaced once the solution becomes cloudy.

Optionally, the calcium soak, rinse, phosphate soak, and additional rinse can be repeated. In some embodiments, the cycle can be repeated for at least 1 and up to about 20 additional cycles.

Once the polymer has been coated with DCPD, it can be converted to an alternative CaP phase, including an octacalcium phosphate, a tricalcium phosphate, a monetite, or an apatite with an aqueous media. The apatite can be further tuned to mimic biological formations. The aqueous media, and any additives used with the media, can determine the coating properties, and the phase of the CaP. Suitable aqueous media include but are not limited to water, a buffer solution, including zwitterionic biological buffer, Good's buffer, HEPEs buffer, Tris buffer, carbonate adjusted buffer, and the like. Additives can include citric acid, fluorine, proteins, calcium, sodium, magnesium, phosphate, and combinations thereof. In some embodiments, the additive can change the structure of the apatite phase. It is possible to have epitaxial growth on the substrate. In some embodiments, one type of mineral can be grown on a second mineral. The material can be used as an implant to provide calcium or other materials to a surface, bone, or other material.

The resulting materials are an aspect of the present invention. The ratio of calcium to phosphate in the resulting materials can be between about 1:1 and about 1:2. The Ca/P value is a defining property of CaP polymorphs, and a Ca/P ratio of 1:1 correlates with DCPD. The significance of the determined Ca/P ratios indicates that the materials can be used to mimic the CaP composition of naturally mineralized tissues including bones and teeth. The variations in particle morphology based on the addition of additives further supports the claim for control over the resulting particle morphologies closely associated with chemical composition.

The materials can be formed into strips, blocks, cylinders, pyramids, or any suitable shape desired. Furthermore, in some embodiments, the material can be formed to a particular shape before or after mineralization.

In some embodiments, the material can further include a second additive that can be included into the material. For example, antimicrobial, antibacterial, antibiotics, cells, growth factors, proteins/peptides, a DNA, a miRNA, a siRNA, a chemokine, or a small molecule drug, other materials or combinations thereof can be incorporated onto or into the material.

A Method to Use a Tunable Apatite Material

An aspect of the invention is a method to use a tunable apatite material. Suitable uses include as a dental material (including crowns, fillings, root canal additives, enamel/dentin remineralization constructs and similar materials), as a bone replacement material, orthopedic applications, treatment of dental carries aimed at remineralizing damaged tissue, or in conjunction with a therapeutic agent for incorporation into a substrate, in permanent or temporary implants (including stents, grafts, catheters, prosthetic devices), biomimetic biodegradable graft materials, void fillers, enhanced interface, regenerative filling materials, restorative filling materials, or the like. In some embodiments, the present invention can be used to cover metallic orthopedic permanent implants. An advantage of the present invention is that the tunable apatite material is biocompatible for use in a patient, human or other animals. Finally, it is possible to use the material of the present invention on the exterior surface coatings to limit biofouling on surfaces, including on aquatic vessels.

An advantage of the tunable apatites of the present invention is that mineralized constructs support cellular activity and have an effect of material induced differentiation of stem cells to bone cell lineages.

A Calcium Phosphate Substrate Precursor

An aspect of the invention is a tunable calcium phosphate substrate precursor. The precursor includes a substrate. The substrate is coated with calcium ions and phosphate ions in the form of DCPD. A phosphate source for the phosphate ions is selected to reduce or eliminate the incorporation of undesirable ions into the precursor. The precursor can be modified into a final product by hydrolyzing the precursor in a solution to make a particular product. For example, to make a product that incorporated fluoride, sodium fluoride can be included in a hydrolyzing fluid.

Characterization of Deposited Calcium Phosphate Hydrogels:

The identity of the incorporated CaP phases was determined by powder X-Ray diffraction (XRD) (Phillips X'pert). Dehydrated polymer samples were directly analyzed over the 2-theta range of 20 to 60° with a step size of 0.02 degrees with Cu-K radiation (A=1.54060 A). Further compositional investigation of the CaP mineral and the PVA hydrogel material was examined by Fourier Transform Infrared Spectroscopy (FTIR, Nexus 470 e.s.p.) over the range of 550-4000 using attenuated total reflectance accessory (Specac, Golden Gate) equipped with a germanium crystal.

The mineral morphology and chemical composition of the CaP-PVA hydrogels before and after hydrolysis was examined by scanning electron microscopy equipped with energy dispersive X-ray spectroscopy (SEM-EDX). Samples were mounted on conductive tape and sputtered with gold. The accelerating voltage was set to 20 kV with a spot size of 4 units. SEM analysis was performed with a Quanta F.E.I 600 using both standard secondary electron and backscatter electron detectors. Line scans of the elemental composition ratios was acquired via EDX with a spot size of 4. Scaffolds were analyzed looking at both the top surface and side face of the material to determine mineral distribution and porosity of the hydrogel.

EXAMPLES

Example 1

Poly(Vinyl) Alcohol Hydrogel

Preparation of Poly Vinyl Alcohol Hydrogels

PVA hydrogels were prepared at 10 wt. % by adding 25 mg of PVA to 225 mL of water maintained at 75° C. under vigorous stirring until polymer was fully dissolved. Solvated PVA was added in 5 mL aliquots to 35 mm circular molds. The molds were then frozen at −80° C. for 24 hours, materials were then removed from the freezer and kept at room temperature until thawed. This freezing cycle was repeated for a total of 5 cycles, with each successive cycle resulting in increased viscosity of the solution and the formation of a physically crosslinked hydrogel. The resulting hydrogel is translucent and swells when immersed in water. PVA hydrogels were stored covered at room temperature until use.

CaP Coating of PVA

Figure 5:
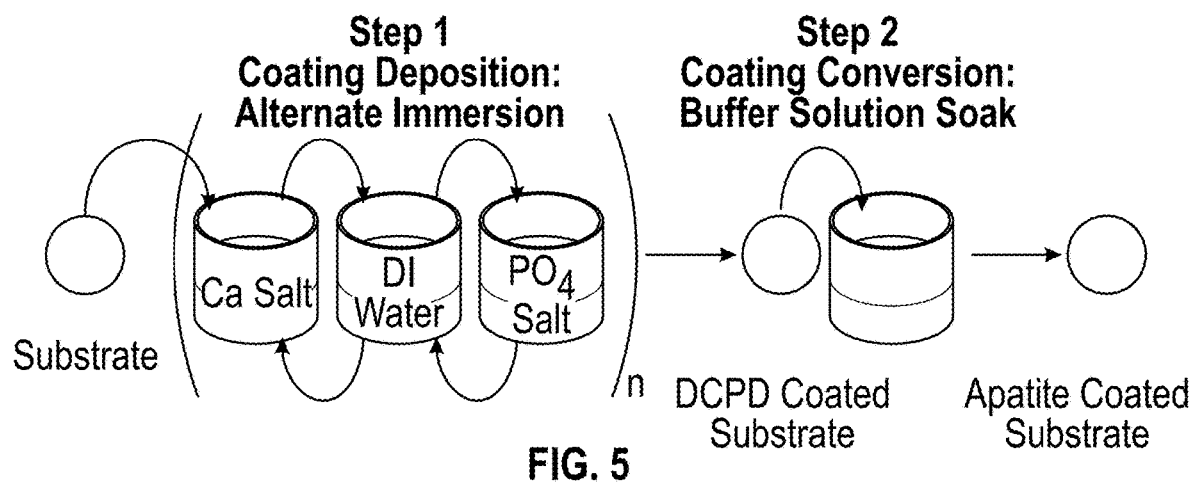
FIG. 5 illustrates a diagram for the deposition and conversion of CaP polymorphs coated on a substrate resulting in the formation of an apatite layer.

The first step of the process is the coating of the selected substrate with a calcium phosphate polymorph by alternate immersion as illustrated in FIG. 5. FIG. 5 illustrates a diagram for the deposition and conversion of CaP polymorphs coated on a substrate resulting in the formation of an apatite layer. In step 1 alternate immersion of the substrate in calcium and phosphate salt solutions deposits the initial DCPD CaP polymorph on the surface of the substrate. In Step 2 the DCPD layer is converted to apatite by soaking in an aqueous buffer solution. The addition of additives to the soak buffer results in variations in the resulting apatite lattice.

The substrate is initially soaked in a solution of 0.25 M Calcium Nitrate for 3 minutes. The substrate is then removed from the Ca solution and rinsed with fresh deionized water. The substrate is subsequently immersed in a 0.25 M Dibasic Potassium Phosphate for an additional 3 min. After soaking in the phosphate solution, the substrate is rinsed again with fresh deionized water. Immersion in both ionic solutions and a final rinse constitutes a single immersion cycle. Additional immersion cycles can be applied to the substrate. Additional immersion cycles result in an increase in the amount of CaP deposited onto the substrate.

Analysis of CaP Coating of PVA

Figure 6:
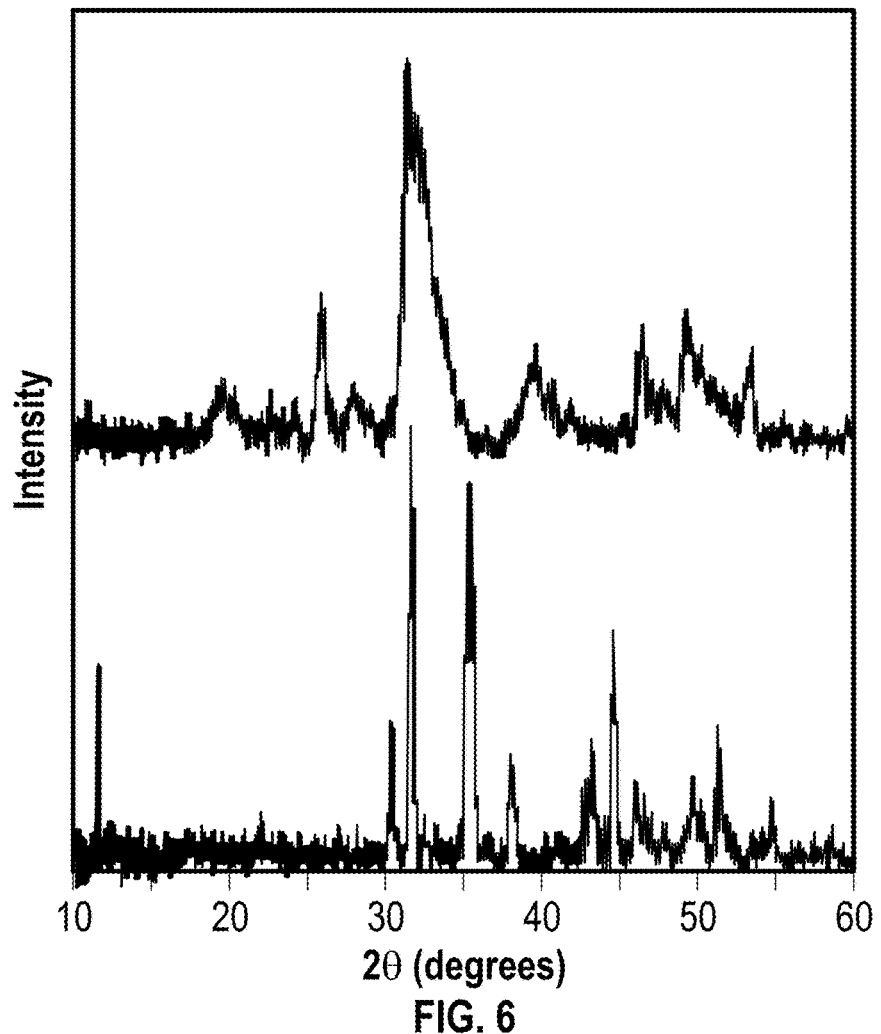
FIG. 6 illustrates XRD patterns of CaP polymorph initially deposited by alternate immersion and following solution hydrolysis (pH 7.4 and 37 C) of the CaP polymorph to apatite.

The identity of the deposited CaP phase on the substrate was determined to be DCPD by powder X-ray diffraction, Fourier Transform Infrared Spectroscopy, and Scanning electron microscopy equipped with energy dispersive X-ray spectroscopy. The CaP polymorph was initially deposited by alternate immersion and following solution hydrolysis at a pH of 7.4 and a temperature of 37C. The IR spectra of calcium phosphates possess unique $PO_4$ stretches in the frequencies between 800-1200 $cm^{-1}$ and can facilitate identification of CaP polymorphs. The CaP phase initially deposited by alternate immersion included 5 distinct peaks at 880, 987, 1058, 1125, and 1210 $cm^{-1}$. These peaks coincide the reported spectra of DCPD. Diffraction patterns illustrated in FIGS. 6 (XRD) and 7 (FTIR) before and after hydrolysis indicate that the CaP polymorph initially deposited is transformed following hydrolysis. Initially deposited. CaP polymorph on the hydrogel possesses key peaks at 12, 29, 31, 35, 45 degrees. Similar to the IR spectra, XRD patterns are unique for each CaP polymorph and represent a crystallographic fingerprint. By comparison with the XRD pattern of CaP polymorphs the deposited CaP polymorph matches the pattern of DCPD.

Figure 7:
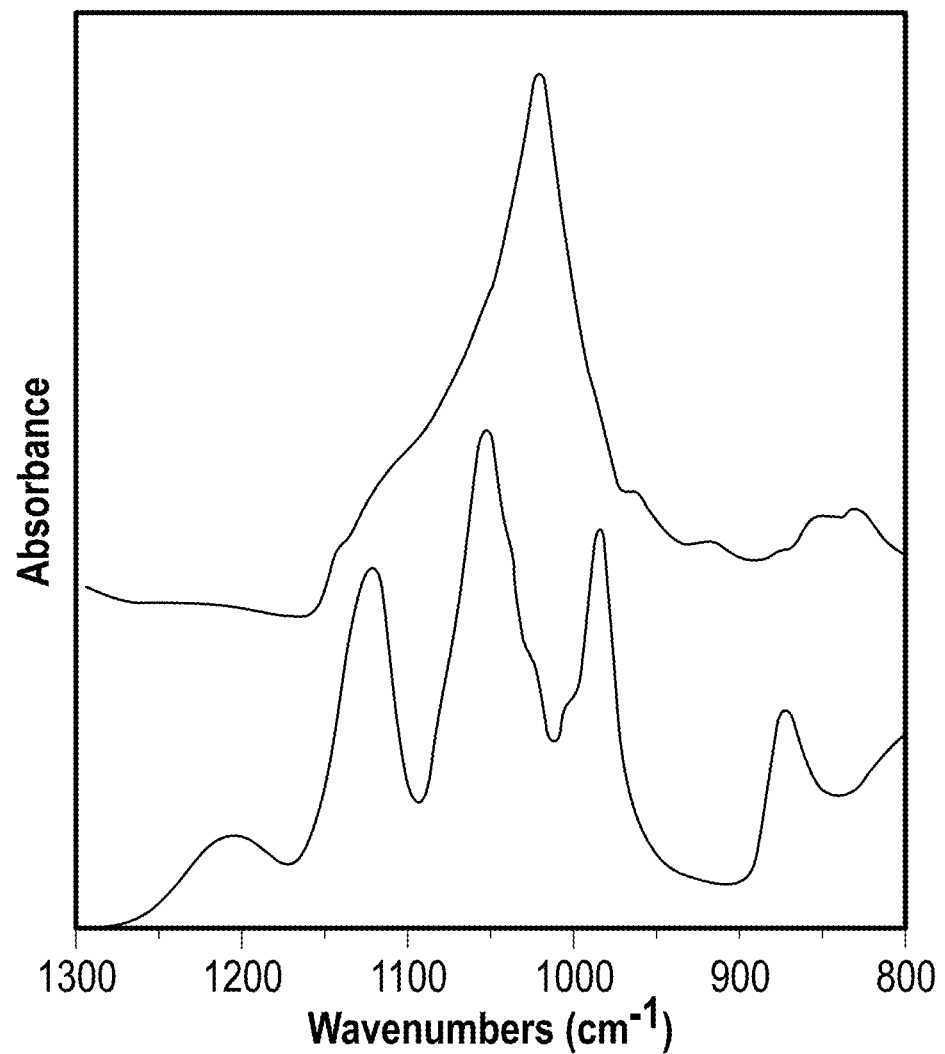
FIG. 7 illustrates FTIR spectra patterns CaP polymorph initially deposited by alternate immersion and following solution hydrolysis (pH 7.4 and 37 C) of the CaP polymorph to apatite.

Conversion of the DCPD polymorph to biogenic apatite proceeds by immersing the CaP coated substrate in an aqueous buffer solution. To mimic biological mineralization transformation of DCPD to apatite, the buffer solution is adjusted to physiological conditions of pH 7.4 and temperature 37° C. The CaP coated substrate is immersed in the buffer solution for 72 h. Periodic adjustment of the pH to return to pH 7.4 is necessary over the course of the reaction. After 72 h no further variations in the hydrolysis solution pH is observed and the reaction is completed. Analysis by FTIR and XRD of the CaP-coated substrate following extended immersion in buffer indicates the initial DCPD CaP coating is transformed to apatite products (illustrated in FIGS. 6 and 7). Corresponding diffraction patterns of the hydrogel indicate a transformation from the initially deposited CaP phase to an apatitic phase following immersion in buffer solutions. Immersion in Tris buffer results in the formation of peaks at 26, 31, and a triplicate cluster at 50 degrees. Each of these peaks are known to correlate with the formation of apatite. However, the low degree of peak resolution is indicative of low crystallinity associated with the formed particles. Transformation to particles with low crystallinity is not uncommon when formed at low temperatures, as is the case with biologically formed apatite. Immersion in Tris buffer results in the transformation of the spectra with a single peak at 1024 cm$^{-1}$ and a minor shoulder at 962 cm$^{-1}$. The conversion to a single peak is consistent with the transformation to apatite.

Figure 8A:
FIG. 8A illustrates SEM images of DCPD particles initially deposited on the surface of the hydrogel at 2000× magnification.
Figure 8B:
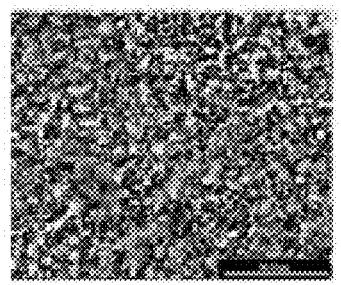
FIG. 8B illustrates SEM images of apatite particles coated on the surface of the substrate following hydrolysis in Tris buffer (pH 7.4 and 37 C) at 2000× magnification.
Figure 8C:
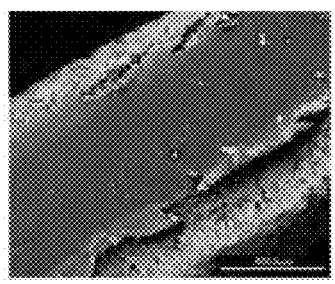
FIG. 8C illustrates a cross sectional SEM images view of the CaP coated hydrogel indicating that particles form exclusively as a surface coating and do not penetrate into the bulk of the hydrogel at 250× magnification.
Figure 9:
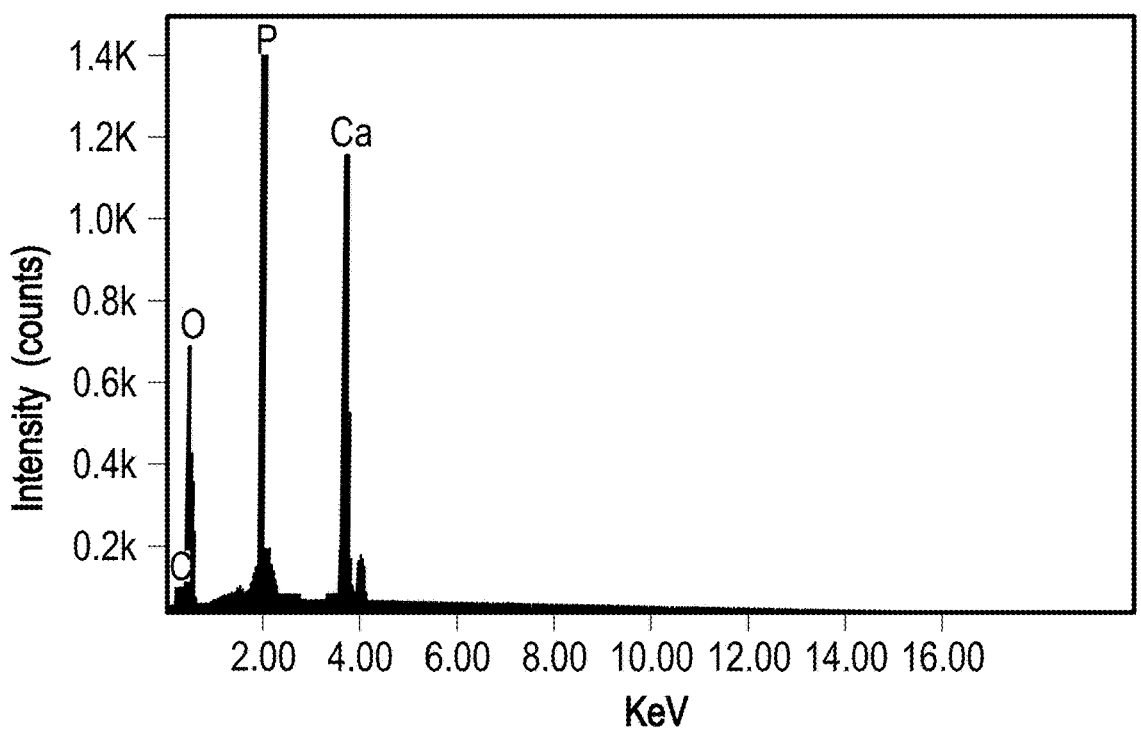
FIG. 9 illustrates a EDX analysis of DCPD coating and apatite coating with CaP ratios of 1.01±0.05.
Figure 10:
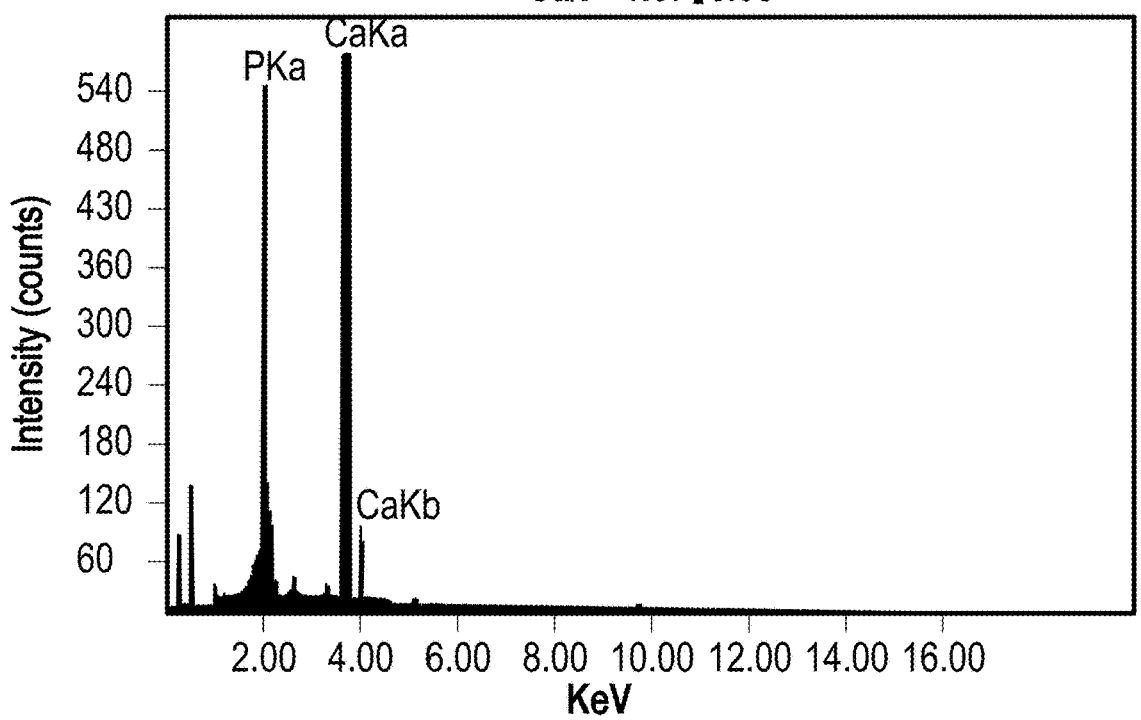
FIG. 10 illustrates a EDX analysis of DCPD coating and apatite coating with CaP ratios of 1.67±0.06.

The morphology of the CaP deposited onto the substrate was visualized by SEM and is illustrated in FIGS. 8A-C. Examination of the hydrogel after alternate immersion indicates the growth of bladed particles emanating from the surface of the material. Cross sectional analysis of the CaP-PVA hydrogel indicates that the CaP is deposited as a coating exclusively on the surface of the material. EDX analysis of the CaP coating on the substrate (illustrated in FIGS. 9 and 10) indicates that the composition of the CaP layer has a Ca/P ratio of 1.01±0.05. FIG. 9 illustrates the EDX analysis of DCPD coating on apatite coating with a CaP ratio of 1.01±0.05, while FIG. 10 illustrates an EDX analysis of a DCPD coating and apatite coating with a CaP ratio of 1.67±0.06. The Ca/P value is a defining property of CaP polymorphs, and a Ca/P ratio of 1.01 correlates with DCPD.

Figure 11:
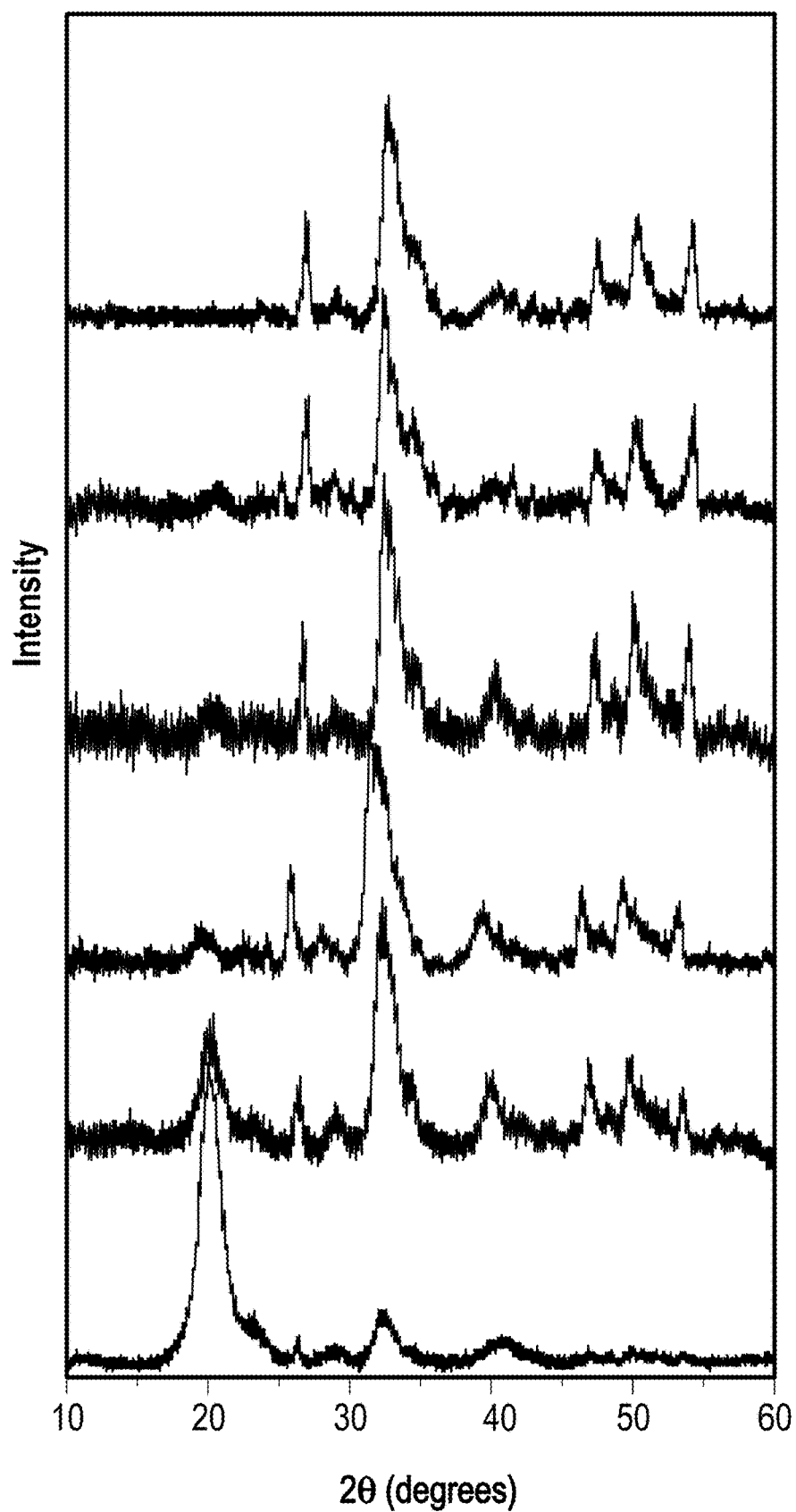
FIG. 11 illustrates XRD patterns of CaP-collagen hydrogel following hydrolysis to apatite based on the number of immersion cycles from bottom to top: 1 cycle, 4 cycles, 8 cycles, 12, cycles, 16, cycles, and 20 cycles.

Analysis of deposition based on the number of alternate immersion cycles (1, 4, 8, 12, 16, and 20 cycles) was examined by monitoring pXRD patterns illustrated in FIG. 11. After a single immersion cycle the incorporation of an apatite phase is detected, although the amounts are minimal as indicated by the low resulting intensities in the diffraction pattern. The formation of apatite phase is clearly evident from 4-20 cycles.

Tuning the Apatite Coating with Hydrolysis Solution Additives

Figure 12:
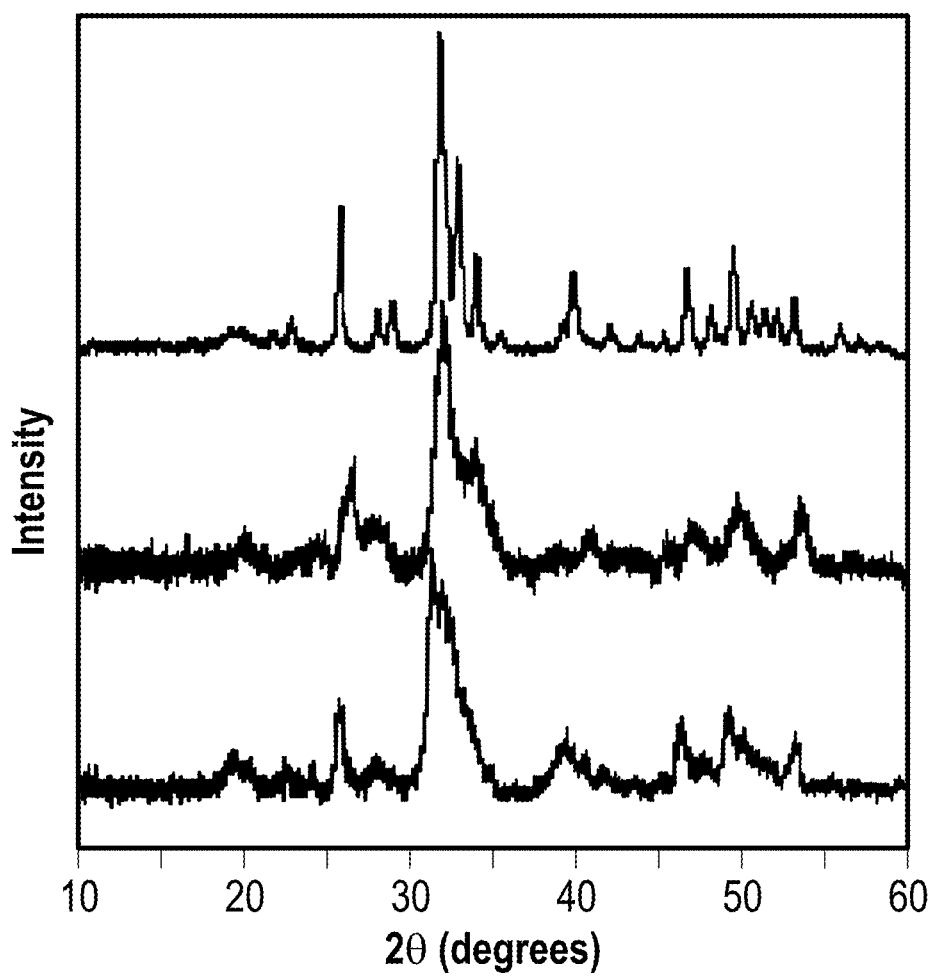
FIG. 12 illustrates XRD patterns of CaP hydrogel after hydrolysis in Tris buffer without additives (bottom) Tris SBF (middle) Tris with added NaF (top)

Tuning the ionic substitution of resulting apatite product is facilitated by the introduction of additives to the hydrolysis buffer solution. In order to introduce fluoride ions into the apatite lattice, NaF is added to the hydrolysis solution. Similarly, to explore the incorporation of additional ions to create a bone-like apatite matrix, the hydrolysis solution consisted of Tris buffer with added salts to form Simulated Body Fluid (SBF). Analysis by XRD of the CaP coated substrate following extended hydrolysis in Tris buffer compared to Tris+F and SBF is illustrated in FIG. 12.

Conversion of the CaP coating to apatite in buffer solutions containing additives in the solution is found to result in deviations in the crystallographic signature of the material. Maturation in SBF results in the increased resolution of the signature apatite peak at 31 degrees with the appearance of an additional peak at 33 degrees attributed to apatite with increased crystallinity of the particles. The introduction of fluoride ions into the immersion buffer results in the formation of highly crystalline CaP particles with exceptional resolution of the apatite peaks observed. The incorporation of F$^-$ ions into the apatite lattice results in the increased crystallinity, as expected since it is known to promote order in the apatite backbone.

Figure 13A:
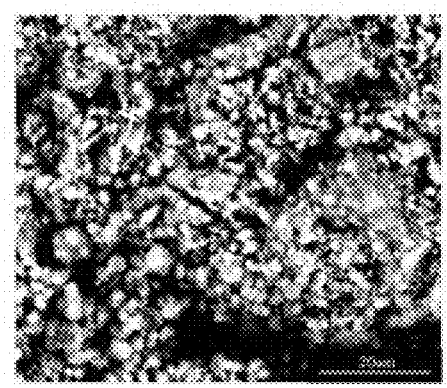
FIG. 13A illustrates a SEM image of CaP coatings following hydrolysis in tris with added fluoride.
Figure 13B:
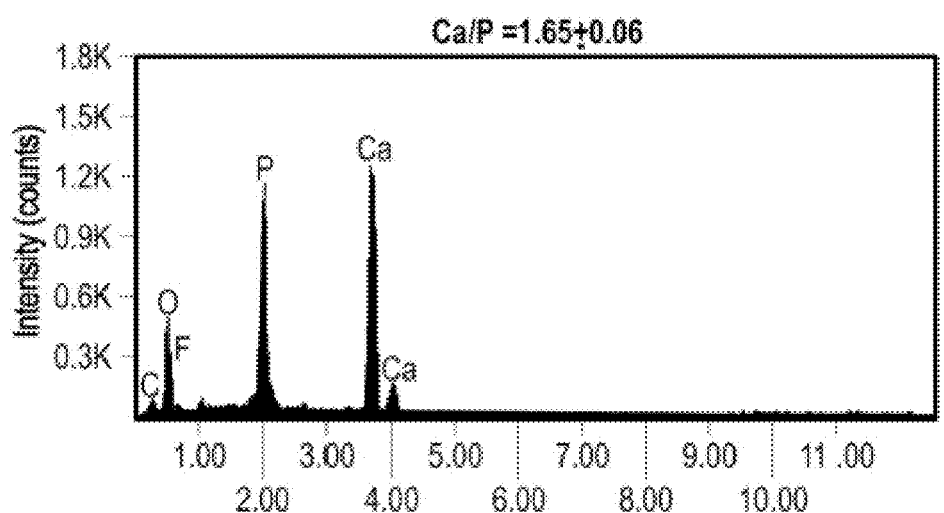
FIG. 13B illustrates a SEM-EDX analysis of CaP coatings following hydrolysis in tris with added fluoride.
Figure 14A:
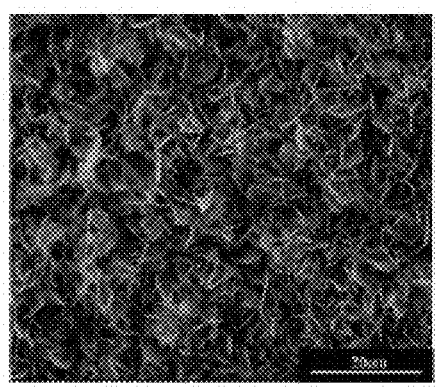
FIG. 14A illustrates SEM image of CaP coatings following hydrolysis in SBF.
Figure 14B:
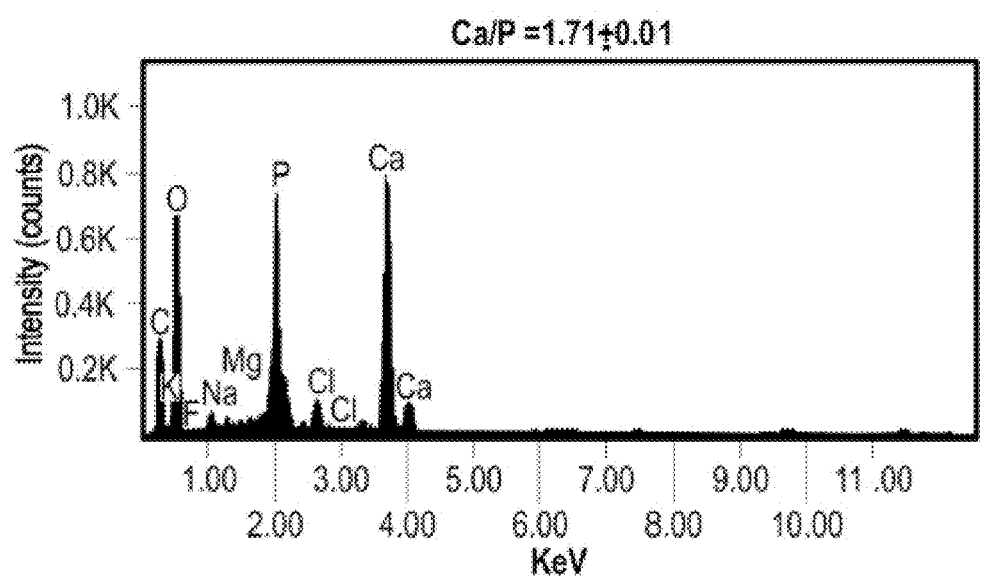
FIG. 14B illustrates a SEM-EDX analysis of CaP coatings following hydrolysis in SBF.

SEM-EDX micrographs of the CaP coated substrates after immersion in the respective solutions are illustrated in FIGS. 13A-B (tris with added fluoride) and FIGS. 14A-B (SBF). Comparison of the resulting CaP coatings indicated a successful transformation from the bladed particles observed for DCPD in all instances. CaP coatings matured in Tris with added NaF resulted in the formation of spherical particles deposited on the substrate. Corresponding EDX analysis indicates a value of Ca/P=1.65±0.01 and the incorporation of F$^-$ ions. CaP conversion in SBF results in the formation of particles clustered on the surface of the material suggestive of a flower petal arrangement. The corresponding EDX analysis indicates the Ca/P=1.71±0.01 and there is evidence of ionic substitution in the lattice with the detection of Na, K, Mg, and Cl in the resulting spectra.

Example Substrate 2

Collagen—Dehydrothermally Crosslinked Hydrogel

Preparation of Collagen Hydrogels

A 0.5 wt. % collagen and 0.05 wt. % chondroitin hydrogel was prepared. Collagen (75 mg) was added to 10 mL of 0.05M acetic acid solution. The collagen solution was kept in an ice bath to prevent denaturing. Separately a solution of chondroitin sulfate (7.5 mg) was prepared in 5 mL of 0.05M acetic acid. The chondroitin solution was added dropwise to the collagen solution while homogenizing at 15,000 rpm over a 30-minute period. Once completely homogenized, the collagen/chondroitin sulfate solution was degassed under vacuum for 60 minutes to remove bubbles introduced during homogenization. Then 3 mL of the collagen solution was transferred into 35 mm circular molds and placed in the freezer at a temperature of about −20° C. for 24 hours. Upon removal from the freezer the samples were lyophilized for 72 h. The lyophilized collagen substrates were then dehydrothermally crosslinked in a vacuum oven at 105° C. for 24 h.

CaP mineralization of collagen occurs according to the stepwise procedure illustrated in FIG. 5, analogous to the coating of synthetic PVA hydrogel. In brief, collagen hydrogels were hydrated in deionized water prior to immersion in Ca-salt solution for 3 min. Collagen immersed in the Ca solution was removed and rinsed in fresh deionized water, immersed in phosphate solution, removed from the phosphate solution and washed in fresh deionized water, which series constitutes a single cycle. Additional cycles resulted in an increase in the amount of white CaP precipitate deposited on the surface leading to an increase in the rigidity of the initially transparent and supple substrate. Following alternate immersion to the desired number of cycles, the CaP-collagen materials were immersed in buffer solution to facilitate the subsequent transformation to apatite.

Figure 15:
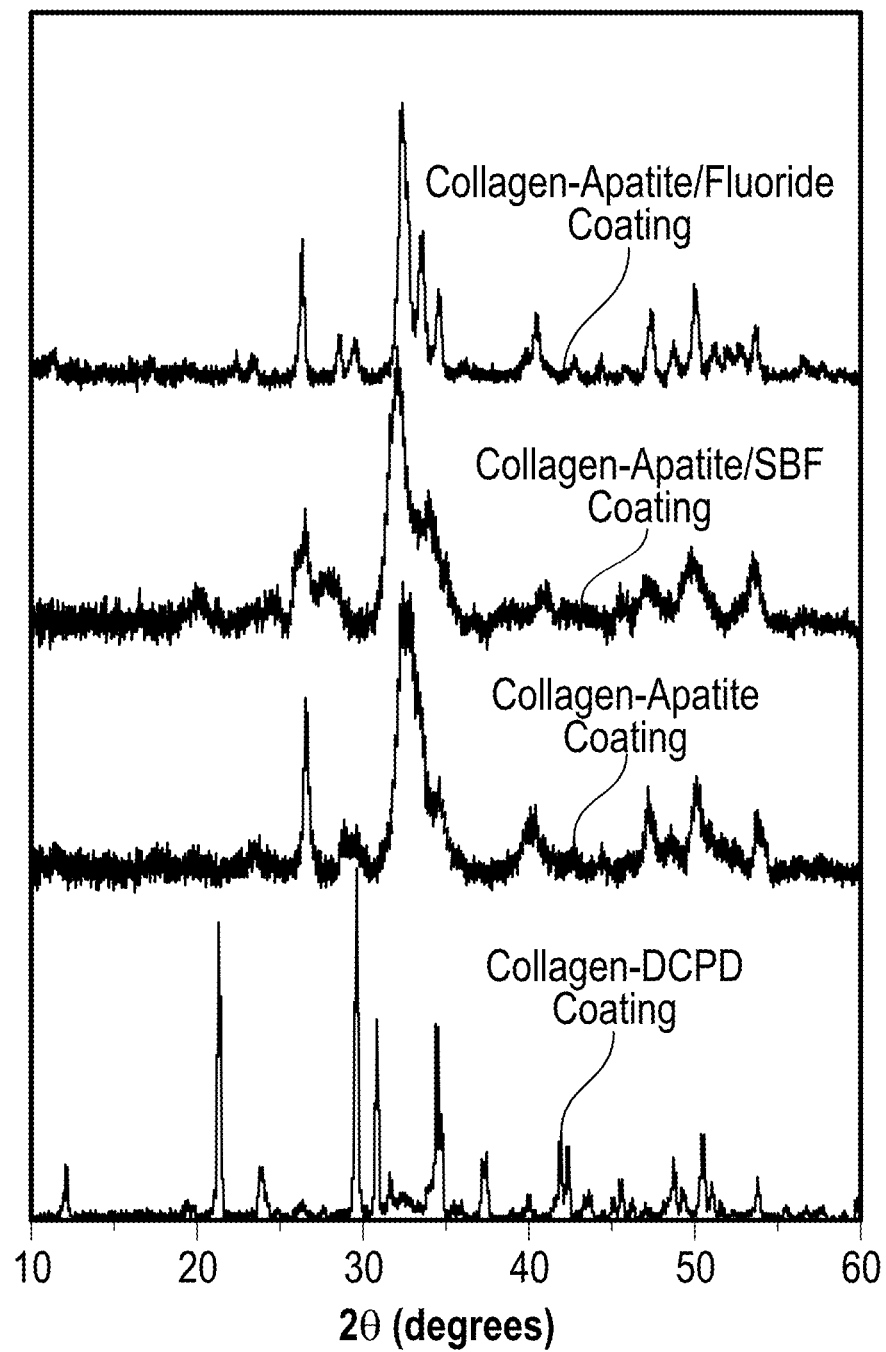
FIG. 15 illustrates XRD patterns of initially deposited DCPD coating on a collagen hydrogel and the transformation to apatite by solution hydrolysis in Tris buffer, Tris buffer with added fluoride, and Tris-SBF solution all maintained at pH 7.4 and 37 C.
Figure 16A:
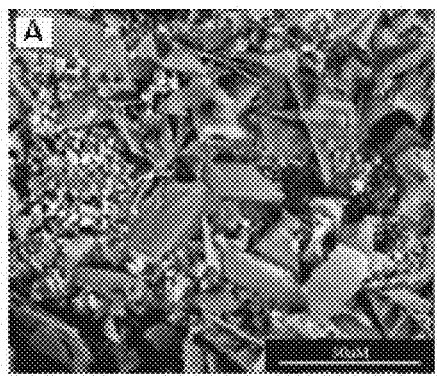
FIG. 16A illustrates SEM images of CaP coated collagen hydrogels—initial CaP coating resulting in the formation of DCPD.
Figure 16B:
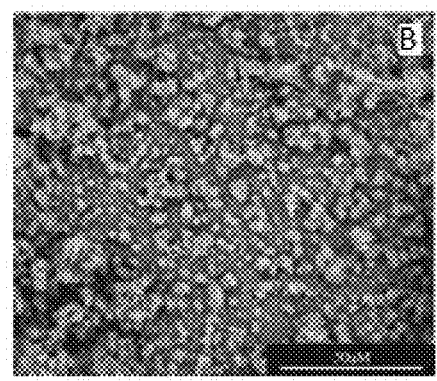
FIG. 16B illustrates SEM images of CaP coated collagen hydrogels—CaP-collagen following hydrolysis in Tris buffer.
Figure 16C:
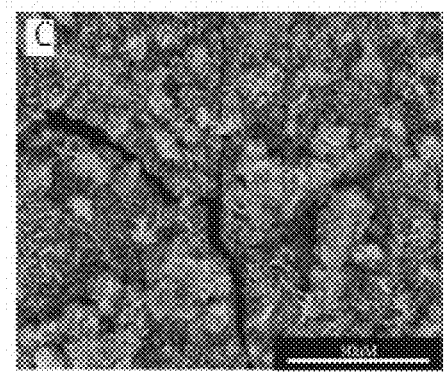
FIG. 16C illustrates SEM images of CaP coated collagen hydrogels—CaP-collagen following hydrolysis in SBF.
Figure 16D:
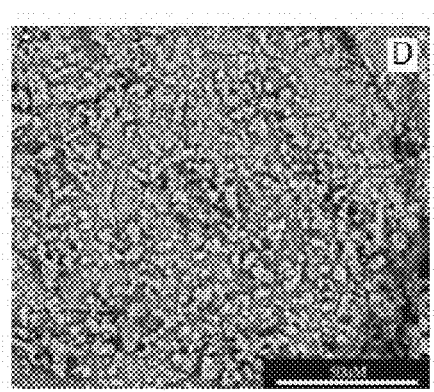
FIG. 16D illustrates SEM images of CaP coated collagen hydrogels—CaP-collagen following hydrolysis in Tris buffer with added NaF.

The CaP coating applied to the collagen substrate was evaluated before and after immersion in the maturation buffer solution. FIG. 15 illustrates XRD patters of initially deposited DCPD coatings on a collagen hydrogel and the transformation to apatite by solution hydrolysis in tris buffer. FIG. 15 also illustrates XRD patterns for samples with fluoride and Tris-SBF hydrolysis solutions. Similar XRD patterns are illustrated for non-collagen samples (see FIG. 12) compared to those for collagen samples. Immersion of the CaP-collagen substrate in Tris buffer results in the transformation of the MUD pattern. This transformation is consistent with the formation of poorly crystalline apatite on the surface of the material. The XRD pattern consists of key peaks at 26, 31, and triplicate peaks centered at 50 degrees. Similar results are observed when the CaP-collagen material is matured in SBF. Immersion in maturation buffer with added fluoride ions results in the formation of apatite phase where the crystallinity is improved based on the appearance of clearly resolved peaks in the pattern. These results are consistent with the incorporation of $F^-$ incorporation into the apatite lattice.

Examination of the CaP-Collagen material by SEM-EDX, which is illustrated in FIGS. 16A-D, indicates that the deposited CaP phase grows as bladed particulates on the surface of the material with a corresponding Ca/P ratio of 1. Following immersion in the buffer solution, transformation of the CaP phase is observed. The morphology and Ca/P ratio of the resulting CaP particles is dependent upon the composition of additives in the maturation buffer solution. In Tris buffer without additional additives, the resulting CaP phase consisted of the formation of CaP sheets grown across the surface with deposits of spherical particulates on the surface. The resulting Ca/P ratio was determined to 1.61±0.16. In contrast, immersion in SBF resulted in the formation of CaP particles grown in clusters of thin elongated strands. EDX analysis indicated the lattice substitution with Na, Mg, K, and Cl ions and a final Ca/P ratio of 1.53±0.23. Lastly, the incorporation of $F^-$ ions into the buffer solution resulted in the formation of dense spherical particles on the material surface. Incorporation of F ions was detected by EDX analysis and the final Ca/P ratio was determined to be 1.66±0.02.

Example 3

Determination of $Ca^{2+}$ and $P_i$ Incorporation

Bulk PVA hydrogels prepared as previously described were transformed into 6 mm×4 mm cylindrical punches that were subsequently coated with for 1-50 deposition cycles. The coated hydrogels from each sample set were split into two groups. Group 1 hydrogels were reserved for immediate analysis by dissolution of the coating in 0.5 mL of 1 M HCl and subsequently diluted to 4 mL with DI water. Group 2 CaP-PVA hydrogels were subjected to conversion treatment in 100 mM Tris buffer for 5 days at 37° C., then dissolved for analysis as described for group 1 samples. The $Ca/P_i$ value is determined by taking the total amount of $Ca^{2+}$ detected and dividing it by the $P_i$ I content.

Quantification of Phosphate

Colorimetric determination of phosphate concentration in the digestion solutions was determined by the formation of a phosphomolybdate complex and measurement by UV-vis spectroscopy at 390 nm. A 0.2 mL aliquot of the analyte solution was reacted with 1.6 mL of Acetone-Acid-molybdate (AAM) solution. The AAM solution was prepared by mixing 25 mL of 10 mM ammonium molybdate tetrahydrate with 25 mL $H_2SO_4$ and 50 mL of acetone. After reacting for 5 min, 0.16 mL of 1 M citric acid was added to the analyte—AAM solution. A standard curve between phosphate concentrations of 1 mM to 2.75 mM was prepared. Analyte solutions outside of this range were diluted with a 1:10 ratio. The resulting phosphate content supplied by the coating was correlated to $mol^1$ $mm^{-2}$. Statistical analysis for significance was computed using the student's t-test (n=4).

Quantification of Calcium

The $Ca^{2+}$ content of the coatings was determined by complex metric titration with EDTA. To prevent precipitation of CaP in solution as the pH is shifted towards alkaline conditions a back titration approach was utilized. In brief, 1 mL of analyte was added to 10 mL of standardized 5 mM EDTA solution. The pH was subsequently increased to 10 by the addition of 1 mL ammonium buffer, followed by the addition of 0.2 mL eriochrome black T (EBT) indicator (0.87 mM EBT in ethanol). Standardized 5 mM $MgCl_2$ solution was titrated into the EDTA solution until the end point was reached by turning the solution from blue to purple. The $Ca^{2+}$ content of the analyte solution was determined by subtracting the amount of $Ca^{2+}$ added from the amount of EDTA added (mol EDTA–mol $Mg_{titrant}$=mol $Ca_{analyte}$).

Figure 17:
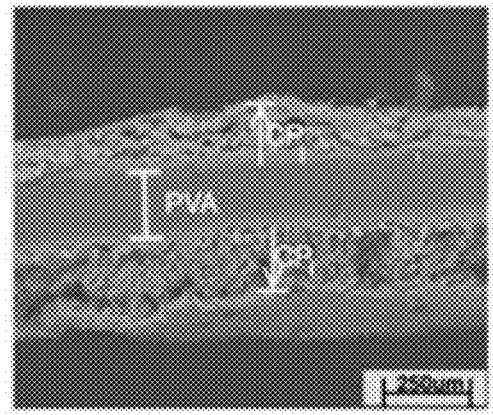
FIG. 17 illustrates deposition and conversion of CaP coating on PVA hydrogel SEM image at 100× magnification of $CP_i$-PVA hydrogel cross section after 20× deposition cycles.
Figure 18A:
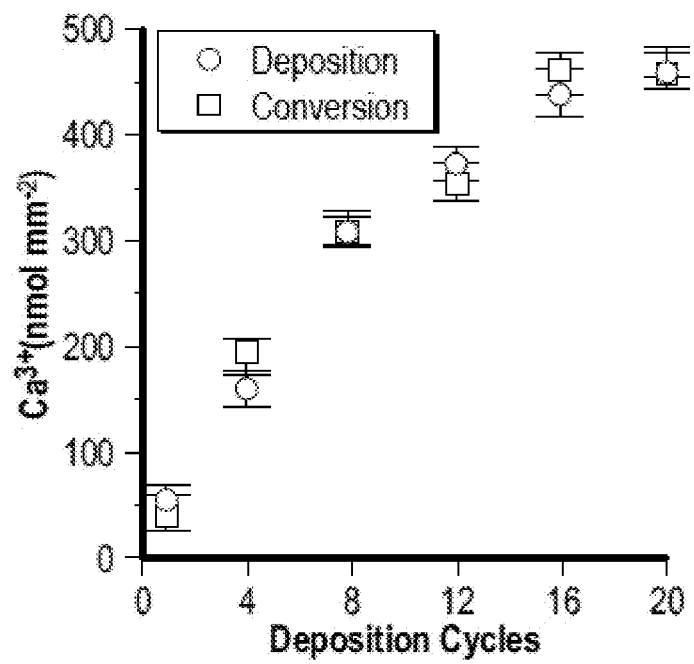
FIG. 18A illustrates $Ca^{2+}$ ionic quantification of surface coatings with increasing deposition cycles for both the initially deposited DCPD coating and after conversion to apatite
Figure 18B:
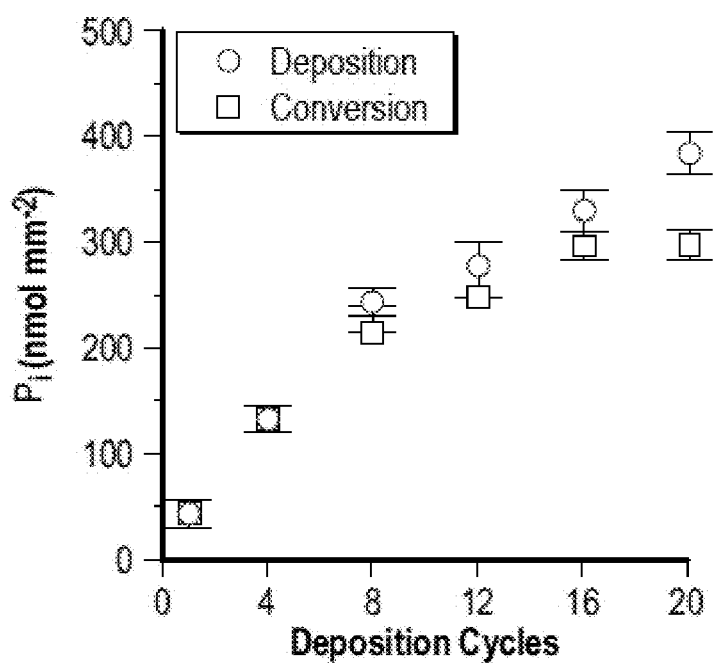
FIG. 18B illustrates $P_i$ ionic quantification of surface coatings with increasing deposition cycles for both the initially deposited DCPD coating and after conversion to apatite.
Figure 19A:
FIG. 19A illustrates a top surface SEM image (2000× magnification) of CaP coatings during the deposition stage for 1 deposition cycle with the corresponding $Ca/P_i$ values.
Figure 19B:
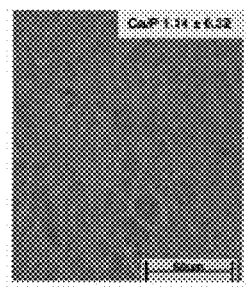
FIG. 19B illustrates a top surface SEM image (2000× magnification) of CaP coatings during the conversion stage for 1 deposition cycle with the corresponding $Ca/P_i$ values.
Figure 19C:
FIG. 19C illustrates a top surface SEM image (2000× magnification) of CaP coatings during the deposition stage for 4 deposition cycles with the corresponding $Ca/P_i$ values.
Figure 19D:
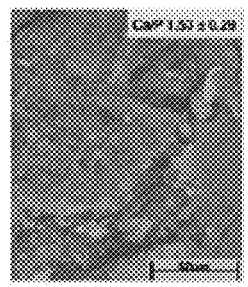
FIG. 19D illustrates a top surface SEM image (2000× magnification) of CaP coatings during the conversion stage for 4 deposition cycles with the corresponding $Ca/P_i$ values.
Figure 19E:
FIG. 19E illustrates a top surface SEM image (2000× magnification) of CaP coatings during the deposition stage for 12 deposition cycles with the corresponding $Ca/P_i$ values.
Figure 19F:
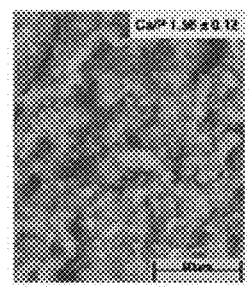
FIG. 19F illustrates a top surface SEM image (2000× magnification) of CaP coatings during the conversion stage for 12 deposition cycles with the corresponding $Ca/P_i$ values.
Figure 19G:
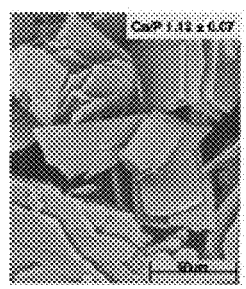
FIG. 19G illustrates a top surface SEM image (2000× magnification) of CaP coatings during the deposition stage for 20 deposition cycles with the corresponding $Ca/P_i$ values.
Figure 19H:
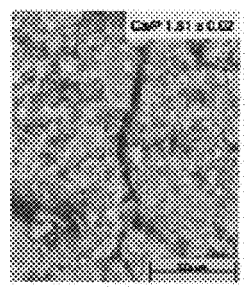
FIG. 19H illustrates a top surface SEM image (2000× magnification) of CaP coatings during the conversion stage for 20 deposition cycles with the corresponding $Ca/P_i$ values.

FIG. 17 illustrates the deposition and conversion of CaP coating on PVA hydrogel SEM image at 100× magnification of $CP_i$-PVA hydrogel cross section after 20× deposition cycles. FIG. 18A illustrates $Ca^{2+}$ and FIG. 18B $P_i$ of ionic quantification of surface coatings with increasing deposition cycles for both the initially deposited DCPD coating and after conversion to apatite. FIGS. 19A-H illustrates a surface SEM images of CaP coatings during deposition and conversion stages for 1 (FIGS. 19A-B), 4 (FIGS. 19C-D), 12 (FIGS. 19E-F), and 20 (FIGS. 19G-H) deposition cycles, with the corresponding $Ca/P_i$ values of each coating shown.

Figure 20A:
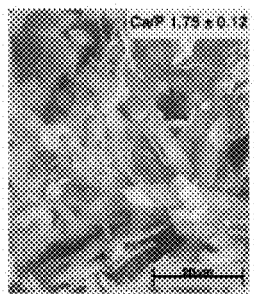
FIG. 20A illustrates a SEM photomicrograph of conversion products when ionic additives are present in the hydrolysis solution with $Ca^{2+}$.
Figure 20B:
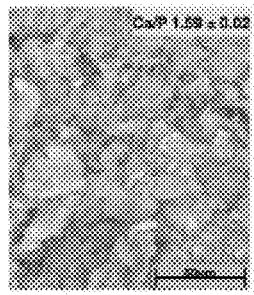
FIG. 20B illustrates a SEM photomicrograph of conversion products when ionic additives are present in the hydrolysis solution with $P_i$.
Figure 20C:
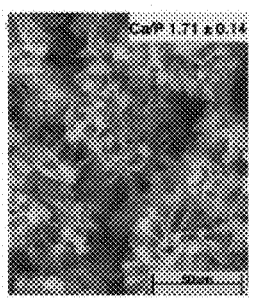
FIG. 20C illustrates a SEM photomicrograph of conversion products when ionic additives are present in the hydrolysis solution with SBF.

The conversion of DCPD (20× deposition) to apatite in the presence of excess $Ca^{2+}$ and $P_i$ ions was investigated as illustrated in FIGS. 20A-D. Under each of the investigated conditions, the particles were converted to apatite, as indicated by the XRD patterns (FIG. 20E) of the conversion products. In the presence of added $Ca^{2+}$ or $P_i$ ions, the diffraction patterns indicated the formation of poorly crystalline apatite coatings. Conversion of DCPD in solutions with added $Ca^{2+}$ or $P_i$ ions resulted in the formation of particles that exhibited enhanced crystal particle growth with well-defined blades coating the surface (FIG. 20A and FIG. 20B). Reaction in SBF where excess $Ca^{2+}$ and $P_i$ ions are simultaneously present resulted in the formation of petal-like particles arranged in clusters on the surface of the hydrogel substrate (FIG. 20C).

The ionic content of the apatite coatings was determined for each condition. Conversion in the presence of excess $Ca^{2+}$ ions results in the increased incorporation of $Ca^{2+}$ ions and consistent $P_i$ incorporation with additive free reactions results in the formation of a Ca-rich apatite coating, with a final resulting $Ca/P_i$ value of 1.75±0.1 (Table 1). The addition of excess $P_i$ ions to the conversion solution was not found to alter the amount of $Ca^{2+}$ or $P_i$ ions incorporated when compared with additive free conversions. Notably conversion in the presence of $Ca^{2+}$ and $P_i$ ions when SBF is used results in an increase in $Ca^{2+}$ ions comparable to $Ca^{2+}$ only conditions, however an increase in $P_i$ content is also observed resulting in a $Ca/P_i$ value maintained at 1.60±1. All values in Table 1 are approximate.

TABLE 1

DCPD Coating Conversion to Apatite in the presence of ionic additives

| Additive [a] | % $Ca^b$ | % $P_i^b$ | $Ca/P_i$ |
|---|---|---|---|
| n/a | 101 ± 4 | 77.9 ± 5 | 1.61 ± 0.02 |
| $Ca^{2+}$ | 117 ± 4 | 80.2 ± 5 | 1.75 ± 0.1 |
| $P_i$ | 100 ± 5 | 73.2 ± 4 | 1.59 ± 0.02 |
| SBF | 115 ± 2 | 87.2 ± 5 | 1.60 ± 0.1 |
| $F^-$ | 102 ± 2 | 72.1 ± 3 | 1.64 ± 0.3 |
| Citrate | 85.3 ± 4 | 60.5 ± 8 | 1.60 ± 0.1 |
| SBF, Citrate | 91.7 ± 4 | 57.4 ± 4 | 1.83 ± 0.1 |

[a] Conversion in Tris buffer pH 7.4, 37° C.
[b] % ions deposited initially as DCPD Thus, the addition of $Ca^{2+}$ and $P_i$ ions to hydrolysis buffer solutions altered the morphologies and the $Ca/P_i$ values of the poorly crystalline apatite coatings. The presence of excess ionic components in the conversion solution enhanced particle growth, because the conversion product was not exclusively dependent on sourcing ions from the initial DCPD coating. However, the exposure to additional ions did not contribute to an increase in the amount of apatite deposited on the surface of the hydrogel. Rather, hydrolysis in excess $Ca^{2+}$ ions resulted in an increase in $Ca^{2+}$ content, with particle growth limited by the lack of additional $P_i$ ions incorporated into the lattice. Similarly, conversion in SBF where $Ca^{2+}$ and $P_i$ ions are simultaneously present did not result in increased mineral deposition; however, the resulting particles were well-defined crystals, indicating that particle growth and resulting morphology can be influenced by the ionic constituents of the conversion buffer solution. In particular, these results offer potential insights into the role of the ionic composition of interstitial fluids during the biosynthesis of apatites found in mature hard tissues.

Conversion in the Presence of Fluoride Ions

Figure 20D:
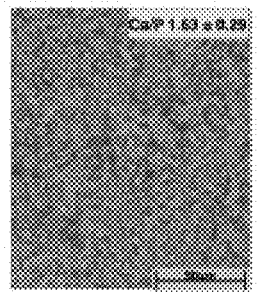
FIG. 20D illustrates a SEM photomicrograph of conversion products when ionic additives are present in the hydrolysis solution with $F^-$.
Figure 20E:
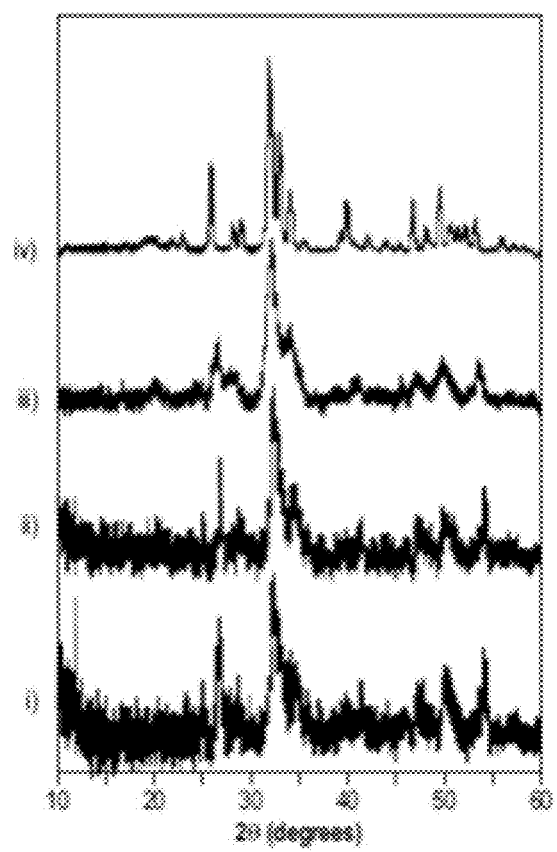
FIG. 20E illustrates XRD spectra of conversion products when ionic additives are present in the hydrolysis solution, i) $Ca^{2+}$, ii) $P_i$, iii) SBF, and iv) $F^-$.

DCPD hydrolysis with $F^-$ ions added to the conversion solution (equation 2) resulted in the formation of small mineral clusters deposited on the hydrogel surface determined to be highly crystalline apatite particles (FIG. 20D). The XRD pattern of the $F^-$ apatite particles indicated the formation of clearly resolved peaks that are consistent with the formation of crystalline hydroxyapatite particles synthesized at high temperatures. Elemental analysis of the coating by accompanying EDX spectroscopy confirmed the incorporation of $F^-$ into the apatite coating. Quantitative analysis of the $F^-$ apatite coatings demonstrated a $Ca/P_i$ value of 1.64±0.3, with the incorporation of $Ca^{2+}$ remaining consistent at 102±4% of the initial coating, but the $P_i$ content decreased to 72.1±3% of the initial coating.

The conversion of DCPD in the presence of $F^-$ ions results in fluorination of the apatite lattice. The $Ca/P_i$ ratio of $F^-$-apatite remained equal to unsubstituted apatite, which is consistent with the known substitution of backbone $OH^-$ ions, leaving the $Ca^{2+}$ and $P_i$ ions unaffected. The smaller ionic radius of $F^-$ ions compared to $OH^-$ are known to enhance crystallinity of the resulting apatite lattice by reducing the distortion along the lattice backbone. Accordingly, diffraction patterns of $F^-$-apatite coatings in this study indicated enhanced crystallinity with clearly resolved apatite peaks present in the diffraction patterns. In addition to improved crystallinity, $F^-$-apatite is known to be less soluble in comparison to its unsubstituted apatite counterpart. In biomineralized enamel, $F^-$ substitution is observed on the outer most surfaces, which is found to play an essential role in the protection against dental carries.

Conversion in the Presence of Citrate Ions

Figure 21A:
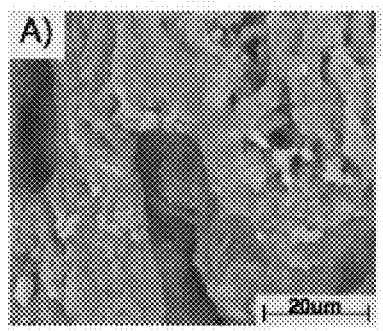
FIG. 21A illustrates SEM photomicrographs of conversion products with citrate ions added to Tris buffer.
Figure 21B:
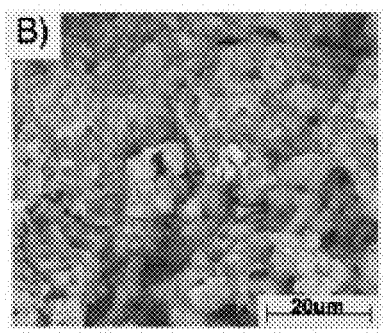
FIG. 21B illustrates SEM photomicrographs of conversion products with citrate ions added to SBF.
Figure 21C:
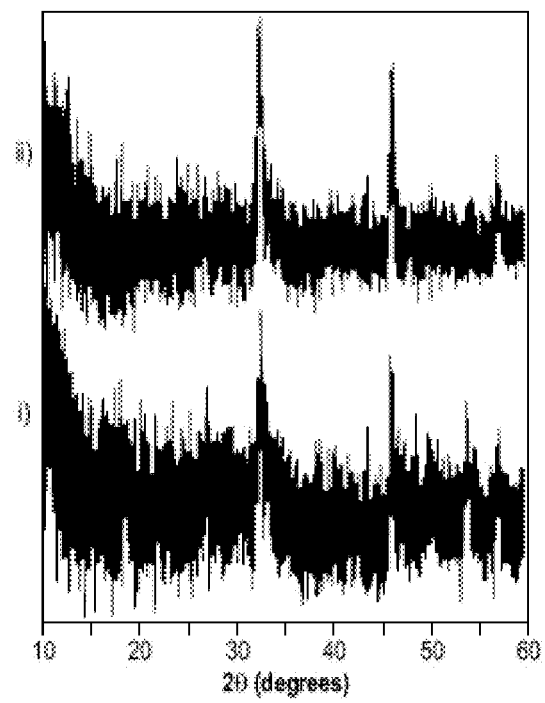
FIG. 21C illustrates XRD patterns of CaP coating conversion with citrate ions in i) Tris and ii) SBF.
Figure 21D:
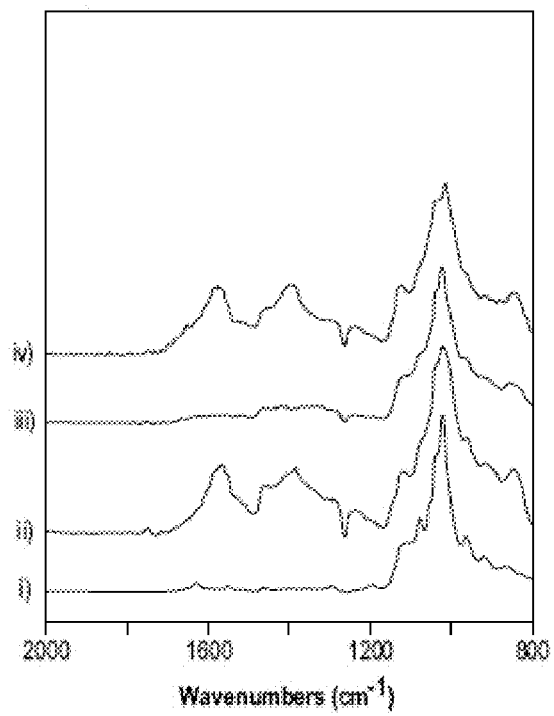
FIG. 21D illustrates ATR-IR spectra of CaP-conversion coating in i) Tris buffer ii) Tris with citrate iii) SBF and iv) SBF with citrate ions.

The addition of citrate ions to the hydrolysis solution for the conversion of DCPD to apatite resulted in the inhibited growth of apatite particles on the surface of the hydrogel substrate as illustrated in FIG. 21A-D. Observation of the particle morphologies by SEM imaging indicated the resulting particles lacked defined crystalline particle features previously observed. Instead, the resulting CaP coatings when citrate was added to either Tris or SBF exhibited restricted crystal growth with flattened surface morphologies and no distinguishable individual particles (FIG. 21A-B). The XRD patterns of the CaP coating on the surface of the hydrogel indicate the successful conversion of the DCPD to apatite, with the resulting product determined to be a poorly crystalline apatite (FIG. 21C). Further analysis of the resulting apatite coatings by ATR-FTIR spectroscopy indicated the presence of incorporated citrate ions with the appearance of peaks between 1200-1600 $cm^-$ (FIG. 21D). These peaks were not observed in apatite conversion products formed without citrate ions. Quantification of the apatite coating formed in the presence of citrate ions demonstrated a decrease in the amount of both incorporated $Ca^{2+}$ and $P_i$ ions (Table 1). Similarly, conversion in SBF with added citrate ions resulted in an increase in the amount of incorporated ions compared to conversion in Tris buffer solutions. Importantly, despite variations in the amount of deposited mineral phase, the $Ca/P_i$ values remained apatitic at 1.60±0.12 and 1.83±0.10 for Tris and SBF conversions, respectively.

During apatite biosynthesis, small organic molecules and large proteins direct in vivo mineral growth. Here citrate molecules are found to direct the growth of apatite particles by restricting both the amount deposited and the three-dimensional particle growth, leading to flat particle morphologies without indication of individual particles. Citrate molecules account for 5.5% of the organic matter of bone apatite and are observed as absorbed species onto the apatite particles. Through adsorption to the surface of the growing apatite mineral, the citrate molecules are found to inhibit crystal growth perpendicular to the surface of the organic substrate. Citrate molecules thus direct the 2D growth of apatite particles into flat plates along the substrate surface during bone formation. Similarly, the conversion of DCPD particles to apatite in the presence of citrate molecules resulted in the formation of apatite coatings with poorly defined particle morphologies and absorbed citrate molecules. The results indicate that the morphologies of the resulting apatite coatings can be readily tuned by the incorporation of directing organic molecules, essential to the preparation of biomimetic apatite coatings.

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of depositing calcium phosphate on a substrate, comprising:
   providing a substrate comprising one of a chitosan, a cellulose, an alginate, a collagen, or combinations thereof;
   immersing the substrate in a calcium ion solution;
   immersing the substrate in water;
   immersing the substrate into a phosphate ion solution;
   alternating the immersion of the substrate into the calcium ion solution and the phosphate ion solution to prepare a coated substrate; and
   tuning the coated substrate to a calcium phosphate by hydrolyzing the coated substrate in a fluid under predetermined physiological conditions to form the calcium phosphate.

2. The method of claim 1, wherein the predetermined physiological conditions of the hydrolyzing comprises a pH of between about 6-10 and a temperature between about 30-50° C.

3. The method of claim 1, wherein the fluid comprises a tris buffer solution, and wherein the tris buffer solution comprises at least one additive selected from the group consisting of a fluoride, a carbonate, a simulated body fluid, a citrate, a calcium ion, a phosphate ion, and a mixed ionic solution to form simulated body fluid, or simulated saliva.

4. The method of claim 1, wherein the substrate is organic or inorganic.

5. The method of claim 1, wherein the substrate further comprises at least one of a PVA, a PEG, a hydrophilic polymer, or combinations thereof.

6. The method of claim 1, wherein the substrate further comprises at least one surface functional group, and wherein the at least one surface functional group comprises at least one of a carboxyl group, a hydroxyl group, a phosphate, or an amino group.

7. The method of claim 1, wherein the substrate further comprises at least one material selected from the group consisting of a silica, a titanium, a gold and combinations thereof.

8. The method of claim 1, further comprising coating the substrate with polydopamine.

9. The method of claim 1, wherein a coating thickness of the coated substrate is tunable to between about 5 μm and about 500 μm.

10. The method of claim 1, wherein a calcium phosphate particle morphology is tunable to a particle shape, a petal like shape, a plate like shape, or a spherical crystal shape.

11. The method of claim 1, further comprising preforming the substrate by cast molding, electrospinning, or 3D printing.

12. The method of claim 1, further comprising an additive, wherein the additive is at least one of an antimicrobial, an antibacterial, an antibiotic, a cell, a growth factor, a protein, a peptide, a DNA, a miRNA, a siRNA, a chemokine, or a small molecule drug.

13. The method of claim 1, further comprising determining a form of the calcium phosphate and choosing a hydrolyzing solution based on the form of the calcium phosphate prior to tuning.

14. The method of claim 13, wherein the determining step occurs after preparing the coated substrate.

15. The method of claim 1, wherein the fluid is a simulated body fluid, a water, a zwitterionic biological buffer solution, a Good's buffer solution, a HEPEs buffer solution, or a carbonate adjusted buffer solution.

16. The method of claim 9, wherein the thickness of the coated substrate is between 125 μm and 500 μm.

17. The method of claim 1, further comprising an additive ionic salt in the fluid, the additive ionic salt comprising at least one of a magnesium, a sodium, a fluoride, a chlorine, a citrate, a carbonate, a calcium, or a phosphate.

18. The method of claim 1, wherein a phosphate source in the phosphate ion solution is a dibasic phosphate compound selected from the group consisting of a dipotassium phosphate, an ammonium phosphate, a phosphoric acid and combinations thereof.

19. The method of claim 1, wherein the calcium source in the calcium ion solution is a calcium salt selected from the group consisting of a calcium chloride, and a calcium nitride.

20. The method of claim 1, wherein the alternating the immersion of the substrate into the calcium ion solution and the phosphate ion solution occurs for between 1 and 21 cycles.

* * * * *